(12) United States Patent
Nakahara et al.

(10) Patent No.: US 8,697,335 B2
(45) Date of Patent: *Apr. 15, 2014

(54) RADIATION-SENSITIVE RESIN COMPOSITION AND COMPOUND

(75) Inventors: Kazuo Nakahara, Tokyo (JP); Mitsuo Sato, Tokyo (JP)

(73) Assignee: JSR Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/351,586

(22) Filed: Jan. 17, 2012

(65) Prior Publication Data

US 2012/0148952 A1 Jun. 14, 2012

Related U.S. Application Data

(63) Continuation of application No. PCT/JP2010/061844, filed on Jul. 13, 2010.

(30) Foreign Application Priority Data

Jul. 17, 2009 (JP) ................. 2009-168405

(51) Int. Cl.
 G03F 7/039 (2006.01)
 G03F 7/004 (2006.01)
 C07D 211/44 (2006.01)
 H01L 21/027 (2006.01)

(52) U.S. Cl.
 USPC ........ 430/270.1; 430/311; 430/326; 430/910; 544/172; 544/389; 546/245; 548/334.1; 548/334.5; 548/374.1; 548/531; 548/562

(58) Field of Classification Search
 None
 See application file for complete search history.

(56) References Cited

U.S. PATENT DOCUMENTS

| 8,273,521 B2 * | 9/2012 | Sato et al. .................. 430/270.1 |
| 2003/0059715 A1 * | 3/2003 | Sato ............................ 430/287.1 |
| 2006/0234154 A1 | 10/2006 | Nishimura et al. |
| 2009/0202945 A1 * | 8/2009 | Nakagawa et al. ........ 430/286.1 |

FOREIGN PATENT DOCUMENTS

| JP | 05-158239 | 6/1993 |
| JP | 05-232706 | 9/1993 |
| JP | 05-249683 | 9/1993 |
| JP | 2001-166476 | 6/2001 |
| JP | 2001-215689 | 8/2001 |
| JP | 2006-227632 | 8/2006 |
| JP | 2006-321770 | 11/2006 |
| JP | 2007-298569 | 11/2007 |
| JP | 2009-199021 | 9/2009 |
| WO | WO 2005/069076 | 7/2005 |
| WO | WO 2006/035790 | 4/2006 |
| WO | WO 2007/116664 A1 * | 10/2007 |

OTHER PUBLICATIONS

JPO English abstract for JP2009-199021 (Saegusa) (2009).*
Machine-assisted English translation for JP2009-199021 (Saegusa) as provided by JPO (2009).*
JPO English abstract for JP2006-321770 (Nagata et al) (2006).*
Derwent English abstract for JP2006-321770 (Nagata et al) (2006).*
Machine-assisted English translation for JP2006-321770 (Nagata et al) provided by JPO (2006).*
International Search Report for corresponding International Application No. PCT/JP2010/061844, Aug. 17, 2010.
Chinese Office Action for corresponding CN Application No. 201080040708.X, Feb. 27, 2013.
Taiwanese Office Action for corresponding TW Application No. 099123288, Mar. 21, 2013.
Japanese Office Action for corresponding JP Application No. 2011-522816, Feb. 4, 2014.

* cited by examiner

*Primary Examiner* — Sin J. Lee

(74) *Attorney, Agent, or Firm* — Ditthavong Mori & Steiner, P.C.

(57) ABSTRACT

A radiation-sensitive resin composition includes a compound, a resin and a radiation-sensitive acid generator. The compound has a structure in which a group represented by a following formula (1) is bound to a nitrogen atom. The resin has an acid-dissociative dissolution-controlling group and has a property such that alkali solubility of the resin increases by an action of an acid. In the formula (1), Y is a monovalent group having 5 to 20 carbon atoms, and "*" represents a bonding hand with the nitrogen atom. In the formula (i), $R^1$, $R^2$ and $R^3$ each independently represent a linear or branched alkyl group having 1 to 4 carbon atoms or a monovalent alicyclic hydrocarbon group having 4 to 12 carbon atoms, or $R^1$ and $R^2$ are linked with each other to form a bivalent alicyclic hydrocarbon group, and "*" represents a bonding hand with the oxygen atom.

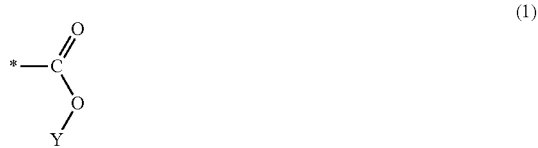

(1)

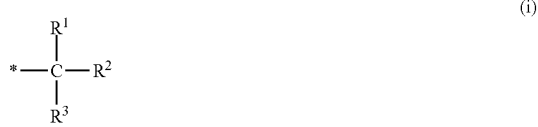

(i)

7 Claims, No Drawings

RADIATION-SENSITIVE RESIN COMPOSITION AND COMPOUND

CROSS-REFERENCE TO RELATED APPLICATIONS

The present application is a continuation application of International Application No. PCT/JP2010/061844, filed Jul. 13, 2010, which claims priority to Japanese Patent Application No. 2009-168405, filed Jul. 17, 2009. The contents of these applications are incorporated herein by reference in their entirety.

BACKGROUND OF THE INVENTION

1. Field of the Invention

The present invention relates to a radiation-sensitive resin composition and a compound.

2. Discussion of the Background

Chemically amplified radiation-sensitive resin compositions generate an acid upon irradiation with an electron beam or far ultraviolet ray typified by KrF excimer laser or ArF excimer laser at a light-exposed site, and a chemical reaction that proceeds with the acid as a catalyst allows the difference in dissolution rates in developing solutions to be produced between the light-exposed site and the light-unexposed site, thereby enabling resist patterns to be formed on the substrate.

As lithography materials for ArF excimer laser that enable microfabrication with light at shorter wavelengths, for example, a resin composition containing as a constitutional component a polymer having in the skeleton an alicyclic hydrocarbon that does not exhibits significant absorption in the area of 193 nm, particularly a polymer having a lactone skeleton in the repeating unit has been used.

A nitrogen-containing compound is added to the aforementioned radiation-sensitive resin composition for the purpose of attaining process stability (see Japanese Unexamined Patent Application, Publication No. H5-232706, Japanese Unexamined Patent Application, Publication No. H5-249683 and Japanese Unexamined Patent Application, Publication No. H5-158239). In addition, for particularly improving lithographic performance of independent patterns, addition of a nitrogen compound having a specific carbamate group has been also studied (see Japanese Unexamined Patent Application, Publication No. 2001-166476 and Japanese Unexamined Patent Application, Publication No. 2001-215689).

However, according to the current situation in which miniaturization of the resist pattern advances to a level of line widths being no greater than 90 nm, not only just improvement of fundamental characteristics such as improvement of resolving ability, expansion of focus, and improvement of rectangularity of the pattern, but also other performance have been demanded. For example, as one of miniaturization techniques of the resist pattern at present, putting liquid immersion lithography into practical applications has been promoted, and a resist material being applicable also to the liquid immersion lithography has been demanded. Specifically, development of a material that satisfies demand characteristics such as a reduction of MEEF (Mask Error Enhancement Factor) that is a marker representing mask error tolerance has been desired.

SUMMARY OF THE INVENTION

According to one aspect of the present invention, a radiation-sensitive resin composition includes a compound, a resin and a radiation-sensitive acid generator. The compound has a structure in which a group represented by a following formula (1) is bound to a nitrogen atom. The resin has an acid-dissociative dissolution-controlling group and a property such that alkali solubility of the resin increases an action of an acid.

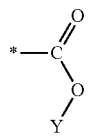

(1)

In the formula (1), Y is a monovalent group having 5 to 20 carbon atoms and represented by a following formula (1), and "*" represents a bonding hand with the nitrogen atom.

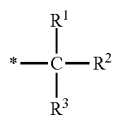

(i)

In the formula (1), $R^1$ and $R^2$ each independently represent a linear or branched alkyl group having 1 to 4 carbon atoms or a monovalent alicyclic hydrocarbon group having 4 to 12 carbon atoms, or $R^1$ and $R^2$ are linked with each other to form a bivalent alicyclic hydrocarbon group having 4 to 12 carbon atoms together with the carbon atom to which $R^1$ and $R^2$ are attached. $R^3$ represents a linear or branched alkyl group having 1 to 4 carbon atoms or a monovalent alicyclic hydrocarbon group having 4 to 12 carbon atoms. "*" represents a bonding hand with the oxygen atom to which Y is bound.

According to another aspect of the present invention, a compound includes structure in which a group represented by a following formula (1) is bound to a nitrogen atom. The compound has a molecular weight of no greater than 3,000.

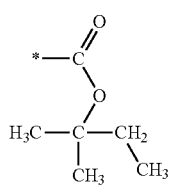

(I)

In the formula (1), "*" represents a bonding hand with the nitrogen atom.

DESCRIPTION OF THE EMBODIMENTS

An embodiment of the present invention provides a radiation-sensitive resin composition containing (A) a compound having a structure in which a group represented by the following formula (1) (hereinafter, also referred to as "group (1)") is bound to a nitrogen atom (hereinafter, also merely referred to as "compound (A)"), (B) a resin having an acid-dissociative dissolution-controlling group, whose alkali solubility increases by the action of an acid (hereinafter, also merely referred to as "resin (B)"), and (C) a radiation-sensitive acid generator (hereinafter, also referred to as "acid generator (C)")

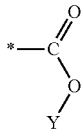

(in the formula (1), Y is a monovalent group having 5 to 20 carbon atoms and represented by the following formula (1); and "*" represents a bonding hand with a nitrogen atom.)

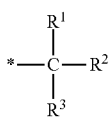

(in the formula (1), $R^1$, $R^2$ and $R^3$ each independently represent a linear or branched alkyl group having 1 to 4 carbon atoms or a monovalent alicyclic hydrocarbon group having 4 to 12 carbon atoms, or $R^1$ and $R^2$ are linked with each other to form a bivalent alicyclic hydrocarbon group having 4 to 12 carbon atoms together with the carbon atom to which they are attached; and "*" represents a bonding hand with an oxygen atom.)

In the radiation-sensitive resin composition, the compound (A) is preferably a compound represented by the following formula (1-1) (hereinafter, also referred to as "compound (A-1)").

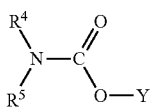

(in the formula (1-1), Y is defined similarly to that in the above formula (1); and $R^4$ and $R^5$ each independently represent a hydrogen atom, a linear or branched alkyl group, a monovalent alicyclic hydrocarbon group, an aryl group or an aralkyl group, alternatively $R^4$ and $R^5$ are linked with each other to form a bivalent heterocyclic group having 4 to 20 carbon atoms together with the nitrogen atom to which they are attached.)

In the radiation-sensitive resin composition, Y in the above formula (1) is preferably a t-amyl group.

In the radiation-sensitive resin composition, the resin (B) preferably has a repeating unit represented by the following formula (3) (hereinafter, also referred to as "repeating unit (3)").

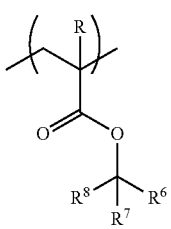

(in the formula (3), R represents a hydrogen atom or a methyl group; $R^6$, $R^7$ and $R^8$ each independently represent a linear or branched alkyl group having 1 to 4 carbon atoms, or a monovalent alicyclic hydrocarbon group having 4 to 20 carbon atoms, alternatively, two among $R^6$, $R^7$ and $R^8$ are linked with each other to form a bivalent alicyclic hydrocarbon group having 4 to 20 carbon atoms together with the carbon atom to which they are attached.)

In the radiation-sensitive resin composition, the resin (B) preferably has a repeating unit that includes at least one selected from the group consisting of a lactone skeleton and a cyclic carbonate skeleton.

The compound of an embodiment of the present invention has a structure in which a group represented by the following formula (I) is bound to a nitrogen atom, and has molecular weight of no greater than 3,000 (hereinafter, also referred to as "compound (A-I)").

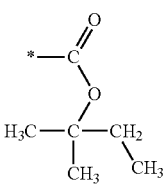

(in the formula (I), "*" represents a bonding hand with a nitrogen atom.)

The aforementioned compound is preferably a compound represented by the following formula (I-1).

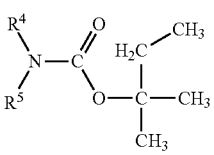

(in the formula (I-1), $R^4$ and $R^5$ each independently represent a hydrogen atom, a linear or branched alkyl group, a monovalent alicyclic hydrocarbon group, an aryl group or an aralkyl group, alternatively $R^4$ and $R^5$ are linked with each other to form a bivalent heterocyclic group having 4 to 20 carbon atoms together with the nitrogen atom to which they are attached.)

According to the radiation-sensitive resin composition of the embodiment of the present invention, a material for chemically amplified resists can be provided which is superior in sensitivity and resolving ability, as well as exhibits satisfactory exposure latitude and MEEF performance.

According to the compound of the embodiment of the present invention, a radiation-sensitive resin composition can be obtained which achieves satisfactory exposure latitude and MEEF performance, in addition to superior sensitivity and resolving ability.

Hereinafter, Description of Embodiments of the present invention is explained, but the present invention is not limited to the following Embodiments.

<Radiation-Sensitive Resin Composition>

The radiation-sensitive resin composition of the embodiment of the present invention contains (A) a compound, (B) a resin and (C) an acid generator and may further contain an optional component. The radiation-sensitive resin composition, due to containing the compound (A) having the above-mentioned specific structure in addition to the resin (B) and the acid generator (C), achieves superior lithographic performance, particularly, excellent exposure latitude and MEEF of the resulting resist. Hereinafter, each constitutional component is sequentially explained.

<Compound (A)>

The compound (A) in the embodiment of the present invention has a structure in which the group (1) is bound to a nitrogen atom. Specifically, included are compounds in which one or more hydrogen atom(s) bound to the nitrogen atom(s) of the compound having one or more amino groups including at least one hydrogen atom bound to a nitrogen atom (hereinafter, also referred to as "amino compound (a)") is/are substituted with the group (1), and the like. The amino compound (a) may have two or more amino groups in which at least one hydrogen atom is bound to a nitrogen atom. In this case, one of hydrogen atoms of these amino groups may be substituted with the group (1), or a plurality of hydrogen atoms may be substituted with the group (1). Furthermore, in the amino group including two or more hydrogen atoms bound to one nitrogen atom, one of the hydrogen atom may be substituted with the group (1), or a plurality of hydrogen atoms may be substituted with the group (1). In this case, Y in the group (1) present in a plurality of numbers in single molecule may be each the same or different.

The compound (A) is a compound in which the group (1) is dissociated by the action of an acid to give a basic amino group, and thus has an effect of improving lithographic performance of the resist obtained from the radiation-sensitive resin composition of the embodiment of the present invention. This effect is remarkable as compared with conventional amine compounds including substitution of the hydrogen atoms with a t-butoxycarbonyl group. This effect is believed to be caused by an improved leaving ability of a leaving group through an increase in the number of carbon atoms of the leaving group as compared with conventional amine compounds having substitution of hydrogen atoms with a t-butoxycarbonyl group, thereby facilitating control of basicity in the resist film, along with suppression of transpiration of substances derived from the leaving group from inside the resist film during prebaking (PB) before the exposure and during post exposure baking (PEB) after the exposure, leading to further improvement of the lithographic performance. The leaving ability of the leaving group is believed to be dependent on stability of the cation assumed to be generated by the action of the acid.

The group (1) is a specific ester group represented by the above formula (1), and is characterized by binding to the end of a —COO— structure, of an acid dissociable hydrocarbon group having 5 to 20 carbon atoms and preferably having 5 to 13 carbon atoms represented by Y in the above formula (1). When Y is a hydrocarbon group having 5 to 20 carbon atoms, dissociation by an acid is likely to occur, whereby lithographic performance can be improved due to facilitated control of basicity in the resist film. In addition, an effect of enabling sublimability of the compound (A) to be reduced is also achieved.

The linear or branched alkyl group having 1 to 4 carbon atoms represented by $R^1$, $R^2$ and $R^3$ in the above formula (i) representing Y is exemplified by a methyl group, an ethyl group, an n-propyl group, an i-propyl group, an n-butyl group, an i-butyl group, and the like. The monovalent alicyclic hydrocarbon group having 4 to 12 carbon atoms represented by $R^1$, $R^2$ and $R^3$, and the bivalent alicyclic hydrocarbon group having 4 to 12 carbon atoms formed together with the carbon atom each attached to $R^1$ and $R^2$ are exemplified by cycloalkanes such as cyclobutane, cyclopentane, cyclohexane, cyclooctane and cyclodecane; groups derived from bridged alicyclic compounds such as norbornane, tricyclodecane, tetracyclododecane and adamantane.

Preferable examples of the monovalent group represented by Y in the above formula (1) include branched alkyl groups such as a t-amyl group, a 1-ethyl-1-methylpropyl group, and a 1,1-diethyl propyl group; and groups having an alicyclic structure represented by the following formulae (i-1) to (i-15). In particular, a t-amyl group is more preferred in terms of ease of synthesis.

(i-1)

(i-2)

(i-3)

(i-4)

(i-5)

(i-6)

(i-7)

(i-8)

(i-9)

-continued

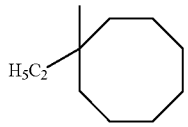
(i-10)

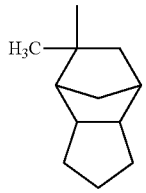
(i-11)

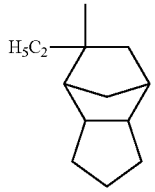
(i-12)

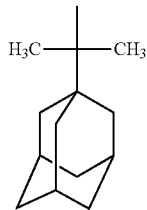
(i-13)

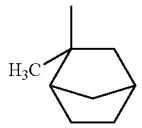
(i-14)

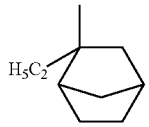
(i-15)

Exemplary amino compound (a) includes a compound represented by the following formula (2) (hereinafter, also referred to as "amino compound (a1)"), a compound having two nitrogen atoms in single molecule (hereinafter, also referred to as "amino compound (a2)"), a compound having three or more nitrogen atoms (hereinafter, also referred to as "amino compound (a3)"), an amide group-containing compound, a urea compound, a nitrogen-containing heterocyclic compound, and the like.

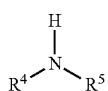
(2)

In the above formula (2), $R^4$ and $R^5$ are as defined in connection with the above formula (1-1), and each independently represent a hydrogen atom, a linear or branched alkyl group, a monovalent alicyclic hydrocarbon group, an aryl group or an aralkyl group, alternatively $R^4$ and $R^5$ may be linked with each other to form a bivalent heterocyclic group having 4 to 20 carbon atoms together with the nitrogen atom to which they are attached.

The linear or branched alkyl group represented by $R^4$ and $R^5$ preferably has 4 or more carbon atoms, and examples thereof include an n-butyl group, an i-butyl group, a sec-butyl group, an n-pentyl group, an n-hexyl group, an n-heptyl group, an n-octyl group, an n-nonyl group, an n-decyl group, and the like. The monovalent alicyclic hydrocarbon group is exemplified by a cyclobutyl group, a cyclopentyl group, a cyclohexyl group, a cyclooctyl group, a norbornyl group, a tricyclodecyl group, a tetracyclododecyl group, an adamantyl group, and the like. The aryl group is exemplified by a phenyl group, a naphthyl group, and the like. Also, the aralkyl group means a lower alkyl group substituted with an aryl group, and specific examples include a benzyl group, a phenylethyl group, a phenylpropyl group, a naphthylmethyl group, a naphthylethyl group, and the like. The bivalent heterocyclic group having 4 to 20 carbon atoms formed by linking of $R^4$ and $R^5$ are with each other together with the nitrogen atom to which they are attached is exemplified by a group having a structure of pyrrole, imidazole, pyrazole, pyrrolidine, piperidine, piperazine, morpholine or the like. It is to be noted that a part or all of the hydrogen atoms included in these groups may be substituted with a hydroxyl group, a carboxyl group, a —COOR group, a —OCOR group (wherein, R represents an alkyl group having 1 to 10 carbon atoms), a cyano group or the like, and in particular, it is preferred that a part of hydrogen atoms of these groups be substituted with a hydroxyl group since sublimation of the compound (A) during a heat treatment can be more suppressed.

Examples of the amino compound (a1) include monoalkylamines such as n-hexylamine, n-heptylamine, n-octylamine, n-nonylamine, n-decylamine and cyclohexylamine; dialkylamines such as di-n-butylamine, di-n-pentylamine, di-n-hexylamine, di-n-heptylamine, di-n-octylamine, di-n-nonylamine, di-n-decylamine, cyclohexyl-methylamine and dicyclohexylamine; aromatic amines such as aniline, N-methylaniline, 2-methylaniline, 3-methylaniline, 4-methylaniline, 2,6-diisopropyl aniline, 4-nitroaniline, diphenylamine, 1-naphthylamine, 2-(4-aminophenyl)-2-(3-hydroxyphenyl)propane and 2-(4-aminophenyl)-2-(4-hydroxyphenyl)propane; alkanolamines such as ethanolamine and diethanolamine; 1-adamantylamines such as 1-adamantylamine and N-methyl-1-adamantylamine, and the like.

Examples of the amino compound (a2) includes 1,2-diaminoethane, 1,4-diaminobutane, 1,6-diaminohexane, 1,7-diaminoheptane, 1,8-diaminooctane, 1,9-diaminononane, 1,10-diaminodecane, 1,12-diaminododecane, 4,4'-diaminodiphenylmethane, 4,4'-diaminodiphenyl ether, 4,4'-diaminobenzophenone, 2,2-bis(4-aminophenyl)propane, 2-(3-aminophenyl)-2-(4-aminophenyl)propane, 1,4-bis[1-(4-aminophenyl)-1-methylethyl]benzene, 1,3-bis[1-(4-aminophenyl)-1-methylethyl]benzene, and the like. Examples of the amino compound (a3) include 4,4'-diaminodiphenylamine, polyallylamine, polymethallylamine, polymers of N-(2-aminoethyl)acrylamide, and the like.

Examples of the amide group-containing compound include formamide, N-methylformamide, acetamide, N-methylacetamide, propionamide, benzamide, pyrrolidone, and the like. Examples of the urea compound include urea, methylurea, 1,1-dimethylurea, 1,3-dimethylurea, 1,3-diphenylurea, tri-n-butylthiourea, and the like. Examples of the nitrogen-containing heterocyclic compound include imidazoles such as imidazole, benzimidazole, 2-methylimidazole, 4-methylimidazole, 2-phenylimidazole, 4-phenylimidazole, 2-phenyl-4-methylimidazole, 2-methyl-4-phenylimidazole, 2-methylbenzimidazole and 2-phenylbenzimidazole, as well as indole, pyrrole, pyrazole, adenine, guanine, purine, pyrrolidine, 2-pyrrolidinemethanol, 3-pyrrolidinol, piperidine, morpholine, 4-hydroxypiperidine, 2,6-dimethyl piperidine, 4-hydroxy-2,6-dimethyl piperidine, 2,2,6,6-tetramethylpiperidine, 4-hydroxy-2,2,6,6-tetramethylpiperidine, piperazine, homopiperazine, 1-methylpiperazine, 1-ethylpiperazine, 2-methylpiperazine, 1-isopropyl piperazine, 1-piperazineethanol, 2,5-dimethyl piperazine, 2,6-dimethyl piperazine, 3-aminopyrrolidine, L-proline, 4-hydroxy-L-proline, pipecolinic acid, nipecotic acid, isonipecotic acid, 2-piperazinecarboxylic acid, 1,4,7-triazacyclononane, 1,4,7,10-tetraazacyclododecane, and the like.

Of these amino compounds (a), the amino compound (a1), the amino compound (a2) and the nitrogen-containing heterocyclic compound are preferred. Moreover, among the amino compounds (a1), dialkylamines and 1-adamantylamines are more preferred, and particularly, di-n-octylamine, di-n-nonylamine, di-n-decylamine, dicyclohexylamine, 1-adamantylamine and N-methyl-1-adamantylamine are still more preferred. Among the amino compounds (a2), 1,6-diaminohexane, 1,7-diaminoheptane, 1,8-diaminooctane, 1,9-diaminononane, 1,10-diaminodecane, 1,12-diaminododecane, and 4,4'-diaminodiphenyl methane are still more preferred. Among the nitrogen-containing heterocyclic compounds, pyrrolidine, piperidine and imidazoles are more preferred, and in particular, pyrrolidine, 2-pyrrolidinemethanol, 3-pyrrolidinol, piperidine, 4-hydroxypiperidine, 4-hydroxy-2,6-dimethyl piperidine, 4-hydroxy-2,2,6,6-tetramethylpiperidine, L-proline, 4-hydroxy-L-proline, benzimidazole, 2-methylimidazole and 2-phenylbenzimidazole are preferred. Also, the conjugate acid of the amino compound (a) has a pKa (measurement temperature: 25° C., the same in the following) of preferably no less than 0. In this case, when a compound whose conjugate acid has a pKa of less than 0 such as for example, an imide compound is used in place of the amino compound (a), resolution and pattern configuration of the resulting resist may be deteriorated.

The compound (A) has a molecular weight of usually 100 to 3,000, preferably 150 to 2,000, and particularly preferably 200 to 1,000. The compound (A) may be used either alone, or as a mixture of two or more thereof.

In the radiation-sensitive resin composition, particularly preferable compound (A) is exemplified by the compound of the embodiment of the present invention (A-I) having a structure in which a t-amyloxycarbonyl group is bound to a nitrogen atom. Specific examples include N-t-amyloxycarbonyl di-n-octylamine, N-t-amyloxycarbonyl di-n-nonylamine, N-t-amyloxycarbonyl di-n-decylamine, N-t-amyloxycarbonyl dicyclohexylamine, N-t-amyloxycarbonyl-1-adamantylamine, N-t-amyloxycarbonyl-N-methyl-1-adamantylamine, N,N-di(t-amyloxycarbonyl)-1-adamantylamine, N-t-amyloxycarbonyl-N-methyl-1-adamantylamine, N,N'-di(t-amyloxycarbonyl)-4,4'-diaminodiphenyl methane, N,N'-di(t-amyloxycarbonyl)-1,6-diaminohexane, N,N,N'N'-tetra(t-amyloxycarbonyl)-1,6-diaminohexane, N,N'-di(t-amyloxycarbonyl)-1,7-diaminoheptane, N,N'-di(t-amyloxycarbonyl)-1,8-diaminooctane, N,N'-di(t-amyloxycarbonyl)-1,9-diaminononane, N,N'-di(t-amyloxycarbonyl)-1,10-diaminodecane, N,N'-di(t-amyloxycarbonyl)-1,12-diaminododecane, N-t-amyloxycarbonyl-pyrrolidine, N-t-amyloxycarbonyl-2-pyrrolidinemethanol, N-t-amyloxycarbonyl-3-pyrrolidinol, N-t-amyloxycarbonyl-piperidine, N-t-amyloxycarbonyl-4-hydroxypiperidine, N-t-amyloxycarbonyl-4-hydroxy-2,6-dimethyl piperidine, N-t-amyloxycarbonyl-4-hydroxy-2,2,6,6-tetramethylpiperidine, N-t-amyloxycarbonyl-L-proline, N-t-amyloxycarbonyl-4-hydroxy-L-proline, N-t-amyloxycarbonyl benzimidazole, N-t-amyloxycarbonyl-2-methylbenzimidazole, N-t-amyloxycarbonyl-2-phenylbenzimidazole, and the like.

The method for synthesizing the compound (A) is as in the following.

After the amino compound (a) and a base (hereinafter, also referred to as "base (b)") are added to a solvent (hereinafter, also referred to as "solvent (s)"), the compound (A) is synthesized by adding thereto a dicarbonic acid compound represented by Y—OCO—O—COO—Y (wherein, Y is as defined in connection with the above formula (1)), or a haloformic acid compound represented by E-COO—Y (wherein, Y is similarly defined to Y in the above formula (1), and E represents any one of a fluorine atom, a chlorine atom, a bromine atom and an iodine atom). It should be noted that the base (b) or the solvent (s) may not be used as the case may be.

After completing the reaction, the compound (A) can be obtained by subjecting to purification through distillation, recrystallization, column chromatography, liquid-liquid cleaning, solid-liquid cleaning or the like as needed.

As the base (b), trimethylamine, triethylamine, tripropylamine, tributylamine, diisopropylethylamine, diisopropylamine, dicyclohexylamine, 1-methylpiperidine, 1-methylpyrrolidine, quinuclidine, 1,4-diazabicyclo[2.2.2]octane, 1,8-diazabicyclo[5.4.0]undeca-7-ene, pyridine, 4-methylpyridine, 2,6-dimethylpyridine, 2,6-diisopropyl pyridine, 2,6-di-t-butylpyridine, lithium hydroxide, sodium hydroxide, potassium hydroxide, sodium carbonate, potassium carbonate, sodium bicarbonate, potassium bicarbonate, lithium, sodium, potassium, lithium hydride, sodium hydride, potassium hydride, calcium hydride, lithium diisopropylamide, n-butyllithium, s-butyllithium, t-butyllithium, sodium-t-butoxide, potassium-t-butoxide or the like may be used. The base (b) may be used either alone, or as a mixture of two or more thereof.

As the solvent (s), heptane, hexane, diethyl ether, dichloromethane, chloroform, tetrahydrofuran, ethyl acetate, dimethyl formamide, dimethylacetamide, dioxane, acetone, methyl ethyl ketone, methyl isobutyl ketone, water or the like may be used. The solvent (s) may be used either alone, or as a mixture of two or more thereof.

With respect to the synthesis carried out using the dicarbonic acid compound, Journal of Medicinal Chemistry 1998, Vol. 41, p. 4983-4994 and the like may be referred to.

With respect to the synthesis carried out using the haloformic acid compound, when, for example, the haloformic acid compound in which E is a chlorine atom, i.e., a chloroformic acid compound is used, the intended compound can be synthesized according to the following scheme. If necessary, the base (b) and the solvent (s) may be also used in each reaction.

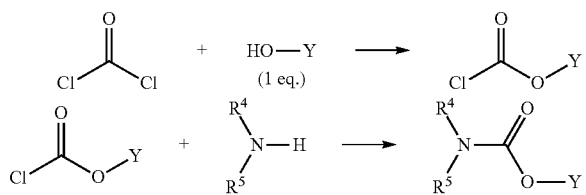

In the above formula, Y is defined similarly to Y in the above formula (1); and "1 eq." means "1 equivalent".

In the radiation-sensitive resin composition, the compound (A) may be used as a mixture with the amino compound (a) not protected with the group (1), or other nitrogen-containing compound such as a tertiary amine compound or a quaternary ammonium hydroxide compound.

Examples of the tertiary amine compound include tri(cyclo)alkylamines such as triethylamine, tri-n-propylamine and tri-n-butylamine; aromatic amines such as N,N-dimethyl aniline; alkanolamines such as triethanolamine and N,N-di (hydroxyethyl)aniline; N,N,N',N'-tetramethylethylenediamine, N,N,N',N'-tetrakis(2-hydroxypropyl)ethylene diamine, bis(2-dimethylaminoethyl)ether, bis(2-diethylaminoethyl)ether, and the like.

Examples of the quaternary ammonium hydroxide compound include tetra-n-propylammonium hydroxide, tetra-n-butylammonium hydroxide, and the like.

The content of the compound (A) in the radiation-sensitive resin composition is preferably 0.01 to 10 parts by mass, more preferably 0.1 to 5 parts by mass, and still more preferably 0.3 to 3 parts by mass with respect to 100 parts by mass of the resin (B). When the content of the compound (A) falls within the above range, the exposure latitude and MEEF performance of the resulting radiation-sensitive resin composition can be further improved.

<Resin (B)>

In the embodiment of the present invention, the resin (B) has an acid-dissociative dissolution-controlling group, and its alkali solubility increases by the action of an acid (but the compound (A) is excluded). The resin (B) is alkali insoluble or hardly alkali soluble before being subjected to the action of the acid. The term "alkali insoluble or hardly alkali soluble" as referred to herein means a property that, when a film produced using only the resin (B) is developed in place of the aforementioned resist film under alkali development conditions employed when resist patterns are formed from the resist film which had been formed with the radiation-sensitive resin composition, no less than 50% of the initial film thickness of the film remains after the development.

The resin (B) is not particularly limited as long as it is a resin having an acid-dissociative dissolution-controlling group, and its alkali solubility increases by the action of the acid. The acid-dissociative dissolution-controlling group is not particularly limited as long as it can be dissociated by the action of the acid, and thus the alkali solubility of the resin (B) thereby increases.

The resin (B) preferably has the repeating unit (3) as a repeating unit that includes an acid-dissociative dissolution-controlling group.

The repeating unit (3) is particularly preferably a repeating unit represented by the following formulae (3-1) to (3-18). The resin (B) may include these alone, or two or more thereof.

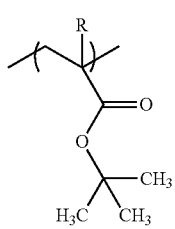

(3-1)

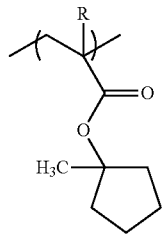

(3-2)

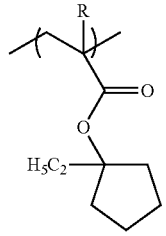

(3-3)

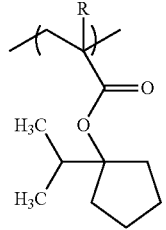

(3-4)

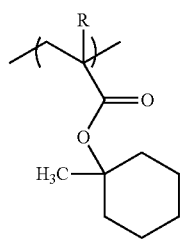

(3-5)

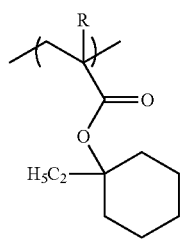

(3-6)

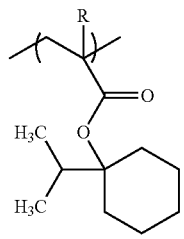

(3-7)

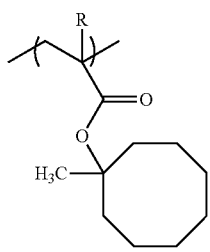 (3-8)
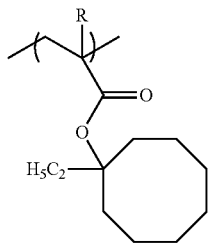 (3-9)
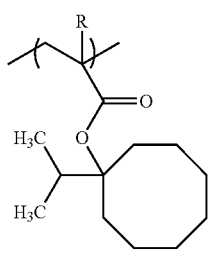 (3-10)
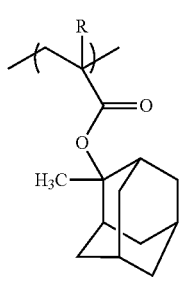 (3-11)
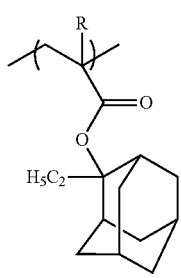 (3-12)
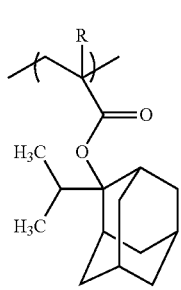 (3-13)
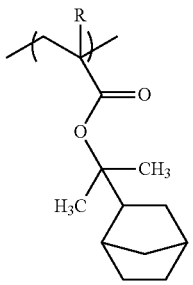 (3-14)
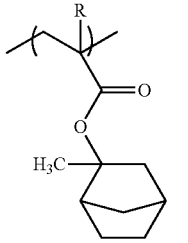 (3-15)
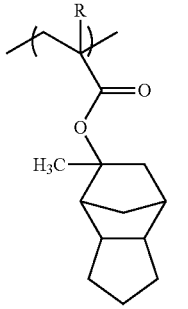 (3-16)
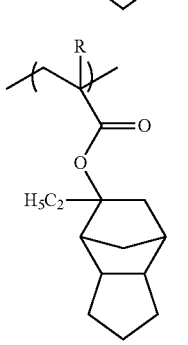 (3-17)
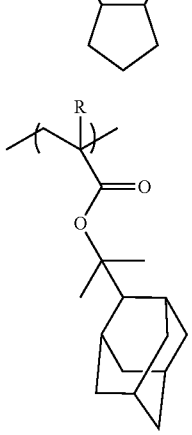 (3-18)
In the above formulae (3-1) to (3-18), R is defined similarly to that in the above formula (3).
In the resin (B), the content of the repeating unit (3) is preferably 5 to 80% by mole and still more preferably 10 to 80% by mole with respect to the entire repeating units constituting the resin (B), and 20 to 70% is particularly preferred. When the content of the repeating unit (3) exceeds 80% by mole, the adhesiveness of the resist film decreases, and thus pattern collapse and pattern peeling may occur.

The resin (B) preferably has a repeating unit that includes at least one skeleton selected from the group consisting of a lactone skeleton and a cyclic carbonate skeleton (hereinafter, also referred to as "repeating unit (4)").

The repeating unit (4) is exemplified by repeating units represented by the following formulae (4-1) to (4-5) as the repeating unit that includes a lactone skeleton, and repeating units represented by the following formula (4-6) as the repeating unit that includes a cyclic carbonate skeleton.

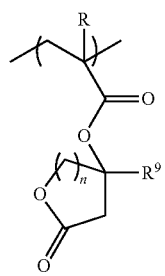
(4-1)

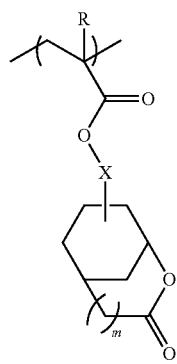
(4-2)

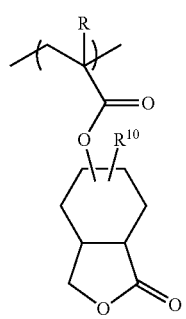
(4-3)

(4-4)

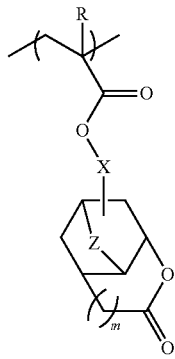
(4-5)

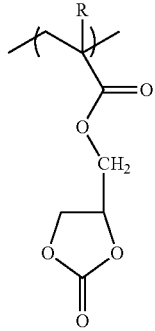
(4-6)

In the above formula (4-1) to (4-6), R represents a hydrogen atom or a methyl group; $R^9$ represents a hydrogen atom or a methyl group; $R^{10}$ represents a hydrogen atom or a methoxy group; X represents a single bond or a methylene group; Z represents a methylene group or an oxygen atom; and n and m are 0 or 1.

The repeating unit represented by the above formula (4-1) is preferably any one of repeating units represented by the following formulae (4-1-1) and (4-1-2). The repeating unit represented by the above formula (4-2) is preferably a repeating unit represented by the following formula (4-2-1). The repeating unit represented by the above formula (4-3) is preferably a repeating unit represented by the following formula (4-3-1). The repeating unit represented by the above formula (4-4) is preferably a repeating unit represented by the following formula (4-4-1). The repeating unit represented by the above formula (4-5) is preferably a repeating unit represented by the following formula (4-5-1).

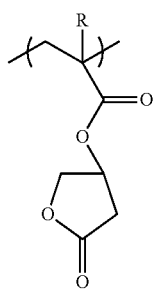
(4-1-1)

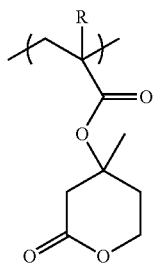
(4-1-2)

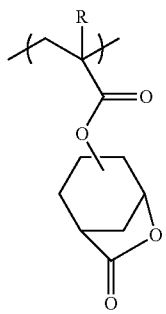
(4-2-1)

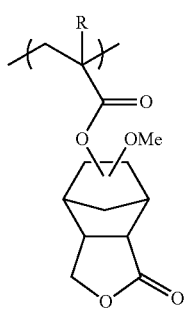
(4-3-1)

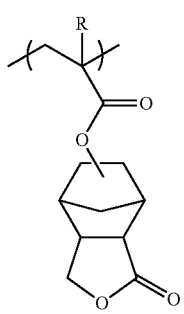
(4-4-1)

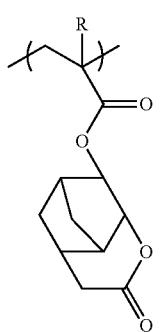
(4-5-1)

In the above formulae (4-1-1), (4-1-2), (4-2-1), (4-3-1), (4-4-1) and (4-5-1), R represents a hydrogen atom or a methyl group.

With respect to the content of the repeating unit (4) in the resin (B), the total amount of the repeating unit (4) with respect to the entire repeating units constituting the resin (B) is preferably 0 to 70% by mole, and more preferably 20 to 60% by mole. By adjusting the content to fall within such a range, developability, defectiveness, low LWR and low PEB temperature dependency as a resist, and the like can be improved. On the other hand, when the content exceeds 70% by mole, resolving ability and LWR as a resist may be deteriorated.

In addition, the resin (B) may have a repeating unit that includes a functional group represented by the following formula.

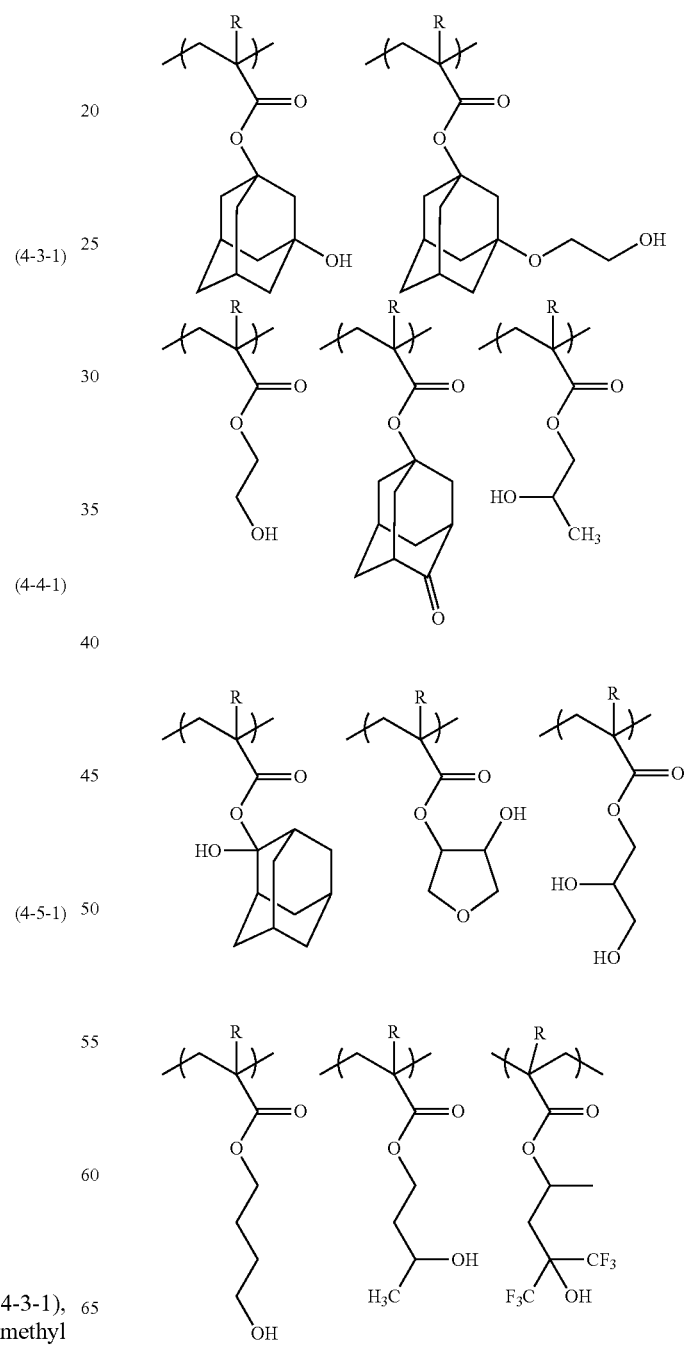

-continued

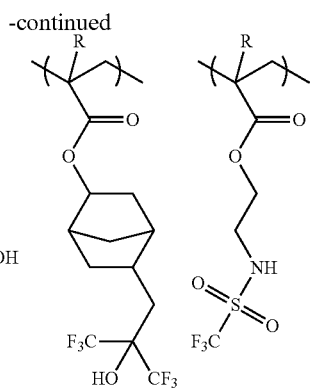

In the above formula, R represents a hydrogen atom or a methyl group.

Furthermore, the resin (B) may also have a repeating unit derived from a (meth)acrylic ester such as methyl (meth)acrylate, ethyl(meth)acrylate, butyl(meth)acrylate, lauryl (meth)acrylate, cyclohexyl(meth)acrylate, (meth)acrylic acid-bicyclo[2.2.1]heptyl ester, (meth)acrylic acid-bicyclo[4.4.0]decanyl ester, (meth)acrylic acid-bicyclo[2.2.2]octyl ester, (meth)acrylic acid-tricyclo[5.2.1.0$^{2,6}$]decanyl ester, (meth)acrylic acid-adamantyl ester or (meth)acrylic acid-tricyclo[3.3.1.1$^{3,7}$]decanyl ester.

The resin (B) may be synthesized in accordance with a routine method such as radical polymerization. For example, the resin (B) is preferably synthesized by a method such as: (1) a method of allowing for a polymerization reaction by adding a solution containing a monomer and a radical initiator dropwise to a solution containing a reaction solvent or a monomer; (2) a method of allowing for a polymerization reaction by separately adding a solution containing a monomer, and a solution containing a radical initiator dropwise to a solution containing a reaction solvent or a monomer; (3) a method of allowing for a polymerization reaction by separately adding a plurality of types of solutions containing each monomer, and a solution containing a radical initiator dropwise to a solution containing a reaction solvent or a monomer; or the like.

It should be noted that when the reaction is allowed by adding to a monomer solution dropwise a monomer solution, the amount of the monomer contained in the monomer solution added dropwise is preferably no less than 30% by mole, more preferably no less than 50% by mole, and particularly preferably no less than 70% by mole with respect to the total amount of the monomer used in the polymerization.

The reaction temperature in these methods may be predetermined ad libitum depending on the type of the initiator. In general, the reaction temperature is 30 to 180° C., preferably 40 to 160° C., and more preferably 50 to 140° C. Time period of dropwise addition may vary depending on conditions involving the reaction temperature, the initiator type, the monomer to be reacted and the like, the time is usually 30 min to 8 hrs, preferably 45 min to 6 hrs, and more preferably 1 to 5 hrs. Also, the entire reaction time including the time period of dropwise addition may vary depending on the conditions similar to the time period of dropwise addition, and is usually 30 min to 8 hrs, preferably 45 min to 7 hrs, and more preferably 1 hour to 6 hrs.

The radical initiator which may be used in the polymerization is exemplified by a 2,2'-azobis(4-methoxy-2,4-dimethylvaleronitrile), 2,2'-azobis(2-cyclopropylpropionitrile), 2,2'-azobis(2,4-dimethylvaleronitrile) and the like. These initiators may be used either alone, or as a mixture of two or more thereof.

As a polymerization solvent, any solvent may be used as long as it is other than solvents that inhibit polymerization (nitrobenzene having a polymerization inhibitory effect, a mercapto compound having a chain transfer effect, etc.), and it can dissolve the monomer. For example, alcohols, ethers, ketones, amides, ester lactones, nitriles and mixed solvents thereof, and the like may be included. These solvents may be used either alone, or as a mixture of two or more thereof.

The resin obtained by the polymerization reaction is preferably recovered by a reprecipitation method. More specifically, after completing the polymerization reaction, the polymerization solution is charged into a reprecipitation solvent to recover the intended resin in the form of powder. As the reprecipitation solvent, the solvents exemplified as the polymerization solvent may be used either alone, or as a mixture of two or more thereof. As an alternative to the reprecipitation method, the resin can be also recovered by a liquid separation operation to remove small-molecule components such as monomer and oligomer. More specifically, after completing the polymerization reaction, the polymerization solution is appropriately concentrated, and thereto is added a solvent system such as e.g., methanol/heptane, selected for separating into two liquids to remove the small-molecule components from the resin solution and appropriately substitute for a necessary solvent system (propylene glycol monomethyl ether, etc.), whereby the intended resin is recovered in the form of a solution.

Although the resin (B) contains low-molecular weight components derived from the monomer, the content thereof is preferably no greater than 0.1% by mass and more preferably no greater than 0.07% by mass with respect to 100% by mass of the total amount of the resin (B), and no greater than 0.05% by mass is particularly preferred.

The content of the low-molecular weight components being no greater than 0.1% by mass can serve in reducing the amount of eluted matter into water brought into contact with the resist film when the resist film is produced using such a resin (B) and subjected to liquid immersion lithography. Furthermore, deposition of foreign substances in the resist can be prevented during storage of the resist, and thus uneven coating is less likely to occur also in resist coating. Therefore, occurrence of defects in forming resist patterns can be sufficiently suppressed.

It should be noted that the "low-molecular weight components" derived from the monomer as referred to herein means components having a polystyrene equivalent weight average molecular weight (hereinafter, may be referred to as "Mw") of no greater than 500 as determined by gel permeation chromatography (GPC). Specifically, the "low-molecular weight components" are components such as monomer, dimer, trimer and oligomer. The low-molecular weight components can be removed by, for example, a chemical purification process such as washing with water and liquid-liquid extraction, a combined process of the chemical purification process with a physical purification process such as ultrafiltration or centrifugal separation, or the like.

Moreover, the low-molecular weight component can be quantitatively determined by an analysis with high performance liquid chromatography (HPLC) on the resin (B). It is preferred that the resin (B) includes impurities such as halogen and metal in addition to the low-molecular weight components, as few as possible, whereby sensitivity, resolution, process stability, pattern configuration and the like achieved when prepared into a resist can be further improved.

On the other hand, although the polystyrene equivalent weight average molecular weight as determined by gel permeation chromatography (GPC) (hereinafter, referred to as "Mw") of the resin (B) is not particularly limited, it is preferably 1,000 to 100,000, more preferably 1,000 to 30,000, and particularly preferably 1,000 to 20,000. The Mw of the resin (B) of less than 1,000 tends to result in deteriorated heat resistance when prepared into a resist. On the other hand, the Mw of the resin (B) exceeding 100,000 is likely to result in deteriorated developability when prepared into a resist.

Furthermore, the ratio (Mw/Mn) of the Mw with respect to the polystyrene equivalent number average molecular weight as determined by gel permeation chromatography (GPC) (hereinafter, referred to as "Mn") of the resin (B) is usually 1.0 to 5.0, preferably 1.0 to 3.0, and more preferably 1.0 to 2.0.

In the radiation-sensitive resin composition of the embodiment of the present invention, the resin (B) may be used either alone, or as a mixture of two or more thereof.

<Acid Generator (C)>

The acid generator (C) in the embodiment of the present invention preferably contains a compound represented by the following formula (C-1).

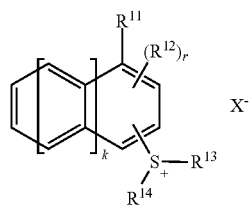

(C-1)

In the above formula (C-1), $R^{11}$ represents a hydrogen atom, a fluorine atom, a hydroxyl group, an alkyl group having 1 to 10 carbon atoms, an alkoxyl group having 1 to 10 carbon atoms, or an alkoxycarbonyl group having 2 to 11 carbon atoms; $R^{12}$ represents an alkyl group having 1 to 10 carbon atoms, an alkoxyl group having 1 to 10 carbon atoms or an alkanesulfonyl group having 1 to 10 carbon atoms; $R^{13}$ and $R^{14}$ each independently represent a an alkyl group having 1 to 10 carbon atoms, a phenyl group or a naphthyl group, alternatively, $R^{13}$ and $R^{14}$ may be linked with each other to form a bivalent group having 2 to 10 carbon atoms; k is an integer of 0 to 2; r is an integer of 0 to 10; and $X^-$ represents an anion represented by the following formulae (c-1) to (c-4):

$R^{15}C_pH_qF_rSO_3^-$: (c-1)

$R^{15}SO_3^-$: (c-2)

in the above formulae (c-1) and (c-2), $R^{15}$ represents a hydrogen atom, a fluorine atom or a hydrocarbon group which has 1 to 12 carbon atoms and which may include a substituent; p is an integer of 1 to 10; q and r are an integer and satisfy the equation of 2p=q+r, wherein r is not 0,

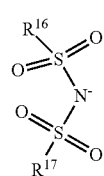

(c-3)

in the above the formula (c-3), $R^{16}$ and $R^{17}$ each independently represent a fluorine-substituted alkyl group having 1 to 10 carbon atoms, and $R^{16}$ and $R^{17}$ may be linked with each other to from a bivalent fluorine-substituted alkylene group having 2 to 10 carbon atoms,

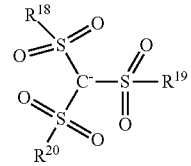

(c-4)

in the above formula (c-4), $R^{18}$, $R^{19}$ and $R^{20}$ each independently represent a fluorine-substituted alkyl group having 1 to 10 carbon atoms; two among $R^{18}$, $R^{19}$ and $R^{20}$ may be linked with each other to from a bivalent fluorine-substituted alkylene group having 2 to 10 carbon atoms.

Examples of the alkyl group having 1 to 10 carbon atoms represented by $R^{11}$ to $R^{14}$ in the above formula (C-1) include in addition to the examples of the alkyl group having 1 to 4 carbon atoms described above, linear alkyl groups such as an n-pentyl group, an n-hexyl group, an n-heptyl group, an n-octyl group, an n-nonyl group and an n-decyl group; branched alkyl groups such as a neopentyl group and a 2-ethylhexyl group; and the like. Of these, a methyl group, an ethyl group, an n-butyl group and a t-butyl group are preferred.

The alkoxyl group having 1 to 10 carbon atoms represented by $R^{11}$ and $R^{12}$ is exemplified by linear alkoxyl groups such as a methoxy group, an ethoxy group, an n-propoxy group, an n-butoxy group and an n-hexyloxy group, branched alkoxyl groups such as an i-propoxy group and an i-hexyloxy group, and the like. Of these, a methoxy group, an ethoxy group, an n-propoxy group and an n-butoxy group are preferred.

The alkoxycarbonyl group having 2 to 11 carbon atoms represented by $R^{11}$ is exemplified by linear alkoxycarbonyl groups such as a methoxycarbonyl group, an ethoxycarbonyl group, an n-butoxycarbonyl group and an n-hexyloxycarbonyl group, branched alkoxycarbonyl groups such as an i-propoxycarbonyl group and an i-hexyloxycarbonyl group, and the like. Of these, a methoxycarbonyl group, an ethoxycarbonyl group and an n-butoxycarbonyl group are preferred.

The alkanesulfonyl group having 1 to 10 carbon atoms represented by $R^{12}$ is exemplified by linear alkanesulfonyl groups such as a methanesulfonyl group, an ethanesulfonyl group, an n-propane sulfonyl group, an n-butanesulfonyl group and an n-hexanesulfonyl group, branched alkanesulfonyl groups such as an i-butanesulfonyl group and an i-hexanesulfonyl group, cycloalkanesulfonyl groups such as a cyclopentanesulfonyl group, a cyclohexanesulfonyl group and a cyclooctanesulfonyl group, and the like. Of these, a methanesulfonyl group, an ethanesulfonyl group, an n-propane sulfonyl group, an n-butanesulfonyl group, a cyclopentanesulfonyl group, and a cyclohexanesulfonyl group are preferred.

Moreover, in the above formula (C-1), r is preferably an integer of 0 to 2.

In the above formula (C-1), the aryl group represented by $R^{13}$ and $R^{14}$ is exemplified by in addition to a phenyl group, substituted phenyl groups such as an o-tolyl group, a m-tolyl group, a p-tolyl group and a 2,3-dimethylphenyl group; groups obtained by substituting a part or all of the hydrogen atoms of these groups with at least one group selected from the set consisting of a hydroxyl group, a carboxyl group, a cyano group, a nitro group, an alkoxyl group, an alkoxyalkyl group, an alkoxycarbonyl group and an alkoxycarbonyloxy group; and the like.

Of the groups that may substitute for the hydrogen atoms of the phenyl group or the substituted phenyl group, the alkoxyl group may include a linear alkoxyl group such as a methoxy group, an ethoxy group, an n-propoxy group or an n-butoxy group; a branched alkoxyl group such as an i-propoxy group, a 2-methylpropoxy group, a 1-methylpropoxy group or a t-butoxy group; a cycloalkyloxy group such as a cyclopentyloxy group or a cyclohexyloxy group, or the like. These groups preferably have 1 to 20 carbon atoms.

The aforementioned alkoxyalkyl group is exemplified by linear alkoxyalkyl groups such as a methoxymethyl group, an ethoxymethyl group, a 2-methoxyethyl group and a 2-ethoxyethyl group; branched alkoxyalkyl groups such as a 1-methoxyethyl group and a 1-ethoxyethyl group; as well as alkoxyalkyl groups having a cycloalkane structure; and the like. These groups preferably have 1 to 20 carbon atoms.

Examples of the alkoxycarbonyl group include linear alkoxycarbonyl groups such as a methoxycarbonyl group, an ethoxycarbonyl group, an n-propoxycarbonyl group and an n-butoxycarbonyl group; branched alkoxycarbonyl groups such as an i-propoxycarbonyl group, a 2-methylpropoxycarbonyl group, a 1-methylpropoxycarbonyl group and a t-butoxycarbonyl group; cycloalkyloxycarbonyl groups such as a cyclopentyloxycarbonyl group and a cyclohexyloxycarbonyl group; and the like. These groups preferably have 2 to 21 carbon atoms.

Examples of the alkoxycarbonyloxy group include linear alkoxycarbonyloxy groups such as a methoxycarbonyloxy group, an ethoxycarbonyloxy group, an n-propoxycarbonyloxy group and an n-butoxycarbonyloxy group; branched alkoxycarbonyloxy groups such as an i-propoxycarbonyloxy group and a t-butoxycarbonyloxy group; cycloalkyloxycarbonyloxy groups such as a cyclopentyloxycarbonyloxy group and a cyclohexyloxycarbonyloxy group; and the like. These groups preferably have 2 to 21 carbon atoms.

The aryl group represented by $R^{13}$ and $R^{14}$ is preferably a phenyl group, a 4-cyclohexylphenyl group, a 4-t-butylphenyl group, a 4-methoxyphenyl group and a 4-t-butoxyphenyl group.

Also, examples of the naphthyl group represented by $R^{13}$ and $R^{14}$ include in addition to a 1-naphthyl group, substituted naphthyl groups such as a 2-methyl-1-naphthyl group, a 3-methyl-1-naphthyl group and a 4-methyl-1-naphthyl group; groups obtained by substituting a part or all of the hydrogen atoms of these groups with at least one group selected from the set consisting of a hydroxyl group, a carboxyl group, a cyano group, a nitro group, an alkoxyl group, an alkoxyalkyl group, an alkoxycarbonyl group and an alkoxycarbonyloxy group; and the like.

The alkoxyl group, alkoxyalkyl group, alkoxycarbonyl group and alkoxycarbonyloxy group that may substitute for the hydrogen atoms of the naphthyl group or substituted naphthyl group may include groups exemplified in connection with the phenyl group described above.

The naphthyl group represented by $R^{13}$ and $R^{14}$ is preferably a 1-naphthyl group, a 1-(4-methoxynaphthyl) group, a 1-(4-ethoxynaphthyl) group, a 1-(4-n-propoxy naphthyl) group, a 1-(4-n-butoxynaphthyl) group, a 2-(7-methoxynaphthyl) group, a 2-(7-ethoxynaphthyl) group, a 2-(7-n-propoxy naphthyl) group and a 2-(7-n-butoxynaphthyl) group.

Further, the bivalent group having 2 to 10 carbon atoms formed by linking of $R^{13}$ and $R^{14}$ with each other is, together with the sulfur atom to which they are attached, a group forming a 5-membered ring or a 6-membered ring with $R^{13}$ and $R^{14}$, and in particular, a group forming a 5-membered ring (tetrahydrothiophene ring) is preferred.

With respect to the bivalent group, a part or all of the hydrogen atoms may be substituted with at least one group selected from the set consisting of a hydroxyl group, a carboxyl group, a cyano group, a nitro group, an alkoxyl group, an alkoxyalkyl group, an alkoxycarbonyl group and an alkoxycarbonyloxy group. The alkoxyl group, alkoxyalkyl group, alkoxycarbonyl group, alkoxycarbonyloxy group may include groups exemplified in connection with the phenyl group described above.

$R^{13}$ and $R^{14}$ are preferably a methyl group, an ethyl group, a phenyl group, a 4-methoxyphenyl group, a 1-naphthyl group, and a group forming a tetrahydrothiophene ring with $R^{13}$ and $R^{14}$ by linking with each other together with the sulfur atom to which they are attached.

The cation in the acid generator (C) represented by the above formula (C-1) is preferably a triphenylsulfonium cation, a tri-1-naphthylsulfonium cation, a tri-tert-butylphenylsulfonium cation, a 4-fluorophenyl-diphenylsulfonium cation, a di-4-fluorophenyl-phenylsulfonium cation, a tri-4-fluorophenylsulfonium cation, a 4-cyclohexylphenyl-diphenylsulfonium cation, a 4-methanesulfonylphenyl-diphenylsulfonium cation, a 4-cyclohexanesulfonyl-diphenylsulfonium cation, a 1-naphthyldimethylsulfonium cation, a 1-naphthyldiethylsulfonium cation, a 1-(4-hydroxynaphthyl)dimethylsulfonium cation, a 1-(4-methylnaphthyl)dimethylsulfonium cation, a 1-(4-methylnaphthyl)diethylsulfonium cation, a 1-(4-cyano naphthyl) dimethylsulfonium cation, a 1-(4-cyano naphthyl) diethylsulfonium cation, a 1-(3,5-dimethyl-4-hydroxyphenyl)tetrahydrothiophenium cation, a 1-(4-methoxynaphthyl)tetrahydrothiophenium cation, a 1-(4-ethoxynaphthyl)tetrahydrothiophenium cation, a 1-(4-n-propoxy naphthyl)tetrahydrothiophenium cation, a 1-(4-n-butoxynaphthyl)tetrahydrothiophenium cation, a 2-(7-methoxynaphthyl)tetrahydrothiophenium cation, a 2-(7-ethoxynaphthyl)tetrahydrothiophenium cation, a 2-(7-n-propoxy naphthyl)tetrahydrothiophenium cation, or a 2-(7-n-butoxynaphthyl)tetrahydrothiophenium cation.

In the above formula (c-1), $-C_pH_qF_r-$ is a fluoroalkylene group which has "p" carbon atoms, and may be either linear or branched; p is preferably 1, 2, 4 or 8; r is preferably an integer of 2 or more; and q may be 0.

In the above formulae (c-1) and (c-2), the hydrocarbon group having 1 to 12 carbon atoms represented by $R^{15}$ is preferably an alkyl group having 1 to 12 carbon atoms, a cycloalkyl group or bridged alicyclic hydrocarbon group.

In the above formulae (c-3) and (c-4), the fluorine-substituted alkyl group having 1 to 10 carbon atoms represented by $R^{16}$ to $R^{20}$ is exemplified by a trifluoromethyl group, a pentafluoroethyl group, a heptafluoropropyl group, a nonafluorobutyl group, a dodecafluoropentyl group, a perfluorooctyl group, and the like.

The bivalent fluorine-substituted alkylene group having 2 to 10 carbon atoms which is formed in the above formula (c-3) by linking of $R^{16}$ and $R^{17}$ with each other, and formed in the above formula (c-4) by linking of two of $R^{18}$ to $R^{20}$ with each other is exemplified by a tetrafluoroethylene group, a hexafluoropropylene group, an octafluorobutylene group, a decafluoropentylene group, an undecafluorohexylene group, and the like.

The anion in the acid generator (C) represented by the above formula (C-1) is preferably a trifluoromethane sulfonate anion, a perfluoro-n-butanesulfonate anion, a perfluoro-n-octanesulfonate anion, a 2-(bicyclo[2.2.1]hepta-2-yl)-1,1,2,2-tetrafluoroethanesulfonate anion, a 2-(bicyclo

[2.2.1]hepta-2-yl)-1,1-difluoroethanesulfonate anion, a 1-adamantyl sulfonate anion, as well as anions represented by the following formulae (c-1-1) and (c-1-2), and the following formulae (c-3-1) to (c-3-7).

(c-1-1)
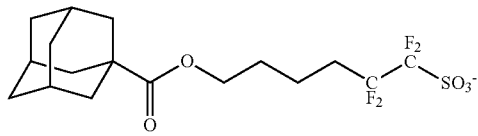

(c-1-2)
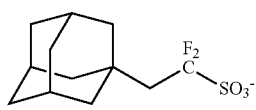

(c-3-1)
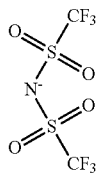

(c-3-2)
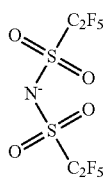

(c-3-3)
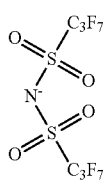

(c-3-4)
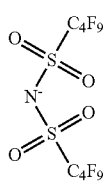

(c-3-5)
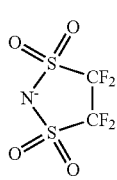

(c-3-6)
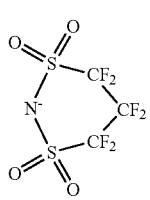

(c-3-7)
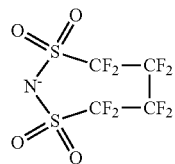

The acid generator (C) may be constituted with, for example, a combination of the cation and anion exemplified above. However, the combination is not particularly limited. In the radiation-sensitive resin composition, the acid generator (C) may be used either of one type alone, or as a mixture of two or more thereof.

Examples of the acid generator (C) include in addition to the acid generator represented by the above formula (C-1), onium salt compounds, halogen-containing compounds, diazo ketone compounds, sulfone compounds, sulfonic acid compounds, and the like. Specifically, the following compounds may be exemplified.

Examples of the onium salt compound include iodonium salts, sulfonium salts, phosphonium salts, diazonium salts, pyridinium salts, and the like.

Examples of the halogen-containing compound include haloalkyl group-containing hydrocarbon compounds, haloalkyl group-containing heterocyclic compounds, and the like.

Examples of the diazo ketone compound include 1,3-diketo-2-diazo compounds, diazo benzoquinone compounds, diazo naphthoquinone compounds, and the like.

Examples of the sulfone compound include β-ketosulfone and β-sulfonylsulfone, and α-diazo compounds of these compounds, and the like.

Examples of the sulfonic acid compound include alkylsulfonic acid esters, alkylsulfonic acid imide, haloalkyl sulfonic acid esters, arylsulfonic acid esters, imino sulfonate, and the like.

These acid generators (C) may be used either alone, or as a mixture of two or more thereof.

The total amount of the acid generator (C) used in the radiation-sensitive resin composition is, in light of securement of the sensitivity and developability as a resist, usually 0.1 to 30 parts by mass, and preferably 0.5 to 20 parts by mass with respect to 100 parts by mass of the resin (B). The total amount of less than 0.1 parts by mass tends to result in deteriorated sensitivity and developability. On the other hand, the total amount exceeding 30 parts by mass leads to reduced transparency for the radioactive ray, and thus tend to results in failure in obtaining a rectangular resist pattern. In addition, the proportion of the acid generator other than the acid generator represented by the above formula (C-1) is preferably no greater than 80% by mass, and more preferably no greater than 60% by mass relative to the total amount of the acid generator (C).

<Solvent (D)>

The radiation-sensitive resin composition of the embodiment of the present invention usually contains (D) a solvent. The solvent employed is not particularly limited as long as it can dissolve at least the compound (A), the resin (B) and the acid generator (C), and (E) an additive as needed. For example, any one of alcohols, ethers, ketones, amides, ester-lactones, nitriles mixed solvents thereof, and the like may be used.

Among these, propylene glycol monoalkyl ether acetates are preferred, and propylene glycol monomethyl ether acetate is particularly preferred. In addition, ketones, alkyl 2-hydroxypropionates, alkyl 3-alkoxypropionates, and γ-butyrolactone are preferred. These solvents may be used either alone, or as a mixture of two or more thereof.

<Additive (E)>

Various types of (E) additives such as a fluorine-containing resin, an alicyclic skeleton compound, a surfactant, and a sensitizer may be included as needed in the radiation-sensitive resin composition. The amount of each additive may be predetermined ad libitum to meet the intended object.

The fluorine-containing resin has an effect of providing water repellency to the surface of the resist film particularly in liquid immersion lithography. Thus, it serves in inhibiting elution of components from the resist film to the liquid immersion liquid, thereby preventing droplets from remaining even if liquid immersion lithography is carried out by fast scanning, and as a result, it achieves an affect of suppressing defects derived from liquid immersion such as water mark and the like.

The structure of the fluorine-containing resin is not particularly limited, and may include: (1) a fluorine-containing resin which is insoluble in a developing solution per se and will be alkali soluble due to the action of an acid; (2) a fluorine-containing resin which is soluble in a developing solution per se and will have increased alkali solubility due to the action of an acid; (3) a fluorine-containing resin which is insoluble in a developing solution per se and will be alkali soluble due to the action of an alkali; and (4) a fluorine-containing resin which is soluble in a developing solution per se and will have increased alkali solubility due to the action of an alkali; and the like.

The fluorine-containing resin is exemplified by a polymer having a fluorine-containing repeating unit. Polymers having the repeating unit (3) described above are preferred.

Examples of the fluorine-containing repeating unit include repeating units derived from trifluoromethyl (meth)acrylate, 2,2,2-trifluoroethyl(meth)acrylate, perfluoroethyl(meth) acrylate and the like.

The fluorine-containing resin is preferably a polymer that includes a combination of, for example, repeating units represented by the following formulae (Ea) to (Ef). These fluorine-containing resins may be used either alone, or as a mixture of two or more thereof.

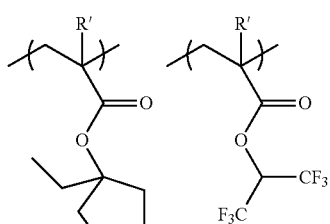
(Ea)

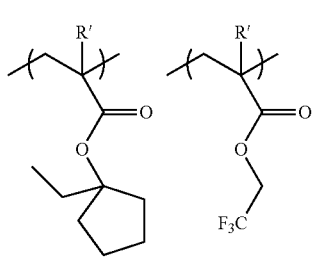
(Eb)

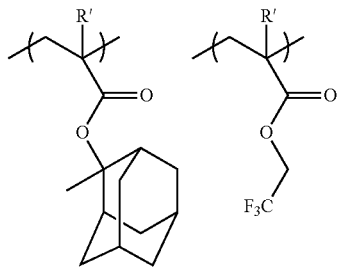
(Ec)

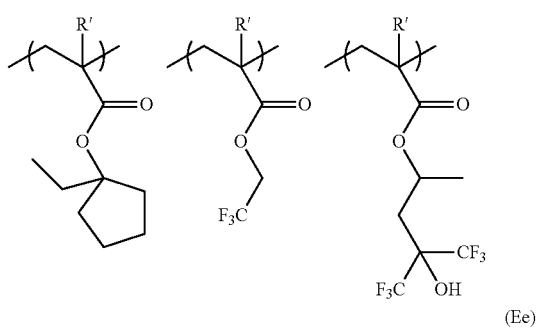
(Ed)

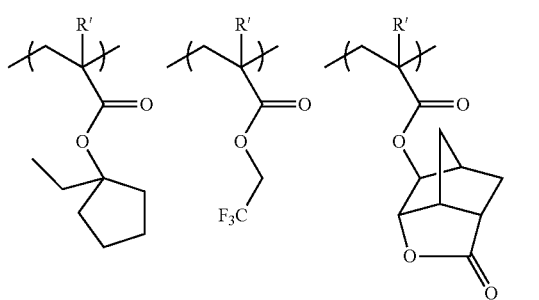
(Ee)

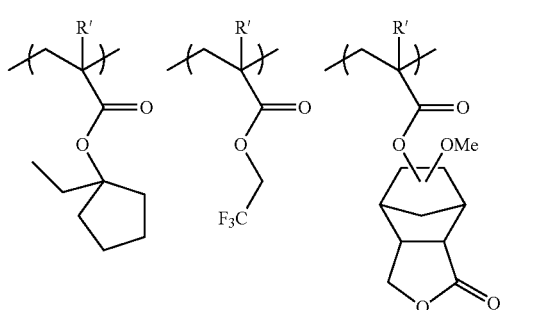
(Ef)

In the above formulae (Ea) to (Ef), R' represents a hydrogen atom or a methyl group.

The alicyclic skeleton compound is a compound which exhibits actions of further improving dry etching resistance, pattern configuration, adhesiveness with the substrate, and the like.

Examples of the alicyclic skeleton compound include adamantane derivatives such as 1-adamantanecarboxylate, 2-adamantanone and t-butyl 1-adamantanecarboxylate; deoxycholic acid esters such as t-butyl deoxycholate, t-butoxycarbonylmethyl deoxycholate and 2-ethoxyethyl deoxycholate; lithocholic acid esters such as t-butyl lithocholate, t-butoxycarbonylmethyl lithocholate and 2-ethoxyethyl lithocholate; 3-[2-hydroxy-2,2-bis(trifluoromethyl)ethyl]tetracyclo[4.4.0.1$^{2,5}$.1$^{7,10}$]dodecane, 2-hydroxy-9-methoxycarbonyl-5-oxo-4-oxa-tricyclo[4.2.1.0$^{3,7}$]nonane, and the like.

These alicyclic skeleton compounds may be used either alone, or as a mixture of two or more thereof.

The surfactant is a component that has an effect of improving coating properties, striation, developability and the like. Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate, as well as all trade names KP341 (manufactured by Shin-Etsu Chemical Co., Ltd.), Polyflow No. 75 and Polyflow No. 95 (manufactured by Kyoeisha Chemical Co., Ltd.), EFTOP EF301, EFTOP EF303 and EFTOP EF352 (manufactured by Tochem Products Corporation), Megaface® F171 and Megaface® F173 (manufactured by Dainippon Ink And Chemicals, Incorporated), Fluorad™ FC430 and Fluorad FC431 (manufactured by Sumitomo 3M Limited), ASAHI GUARD AG710, Surflon S-382, Surflon SC-101, Surflon SC-102, Surflon SC-103, Surflon SC-104, Surflon SC-105 and Surflon SC-106 (manufactured by Asahi Glass Co., Ltd.), and the like. These surfactants may be used either alone, or as a mixture of two or more thereof.

The sensitizer serves in absorbing the energy of radioactive rays, and transferring the energy to the acid generator (C), thereby increasing the amount of acid generation, and thus has an effect of improving "apparent sensitivity" of the radiation-sensitive resin composition.

Examples of the sensitizer include carbazoles, acetophenones, benzophenones, naphthalenes, phenols, biacetyl, eosin, rose bengal, pyrenes, anthracenes, phenothiazines, and the like. These sensitizers may be used either alone, or as a mixture of two or more thereof.

As the additive (E), a dye, a pigment, an adhesion promoter and the like may be also used. By using, for example, a dye or pigment, a latent image of the light-exposed site is visualized, whereby influences of halation upon exposure can be mitigated. In addition, by including an adhesion promoter, adhesiveness with the substrate can be enhanced. Also, further examples of the additive (E) include in addition to the foregoings, an alkali soluble resin, a low molecular alkali solubility controlling agent having an acid dissociable protecting group, a halation inhibitor, a storage stabilizing agent, a defoaming agent, and the like.

It should be noted that as the additive (E), various types of additives described in the foregoing may be used either alone, or two or more thereof may be used in combination.

<Preparation Method of Radiation-Sensitive Resin Composition>

The radiation-sensitive resin composition of the embodiment of the present invention is generally prepared upon use as a solution of the radiation-sensitive resin composition by dissolving in the solvent (D) so as to give the total solid content of usually 1 to 50% by mass, and preferably 2 to 25% by mass, followed by filtration with a filter having a pore size of, for example, about 0.2 μm.

<Method for Forming Photoresist Pattern>

The radiation-sensitive resin composition of the embodiment of the present invention is useful as a chemically amplified resist. In a chemically amplified resist, due to an action of the acid generated from an acid generator (C) upon exposure, a resin component, predominantly an acid-dissociative dissolution-controlling group in the resin (B) is dissociated to generate a carboxyl group or the like. As a result, solubility of the resist at light-exposed sites in an alkaline developer increases, whereby the light-exposed sites are dissolves in the alkaline developer and removed. Accordingly, a photoresist pattern of positive type, etc., is obtained.

According to the method for forming a photoresist pattern, a photoresist pattern is generally formed, for example, as shown in the following. More specifically, a photoresist pattern can be formed by (1) using the radiation-sensitive resin composition to form a photoresist film on a substrate (hereinafter, may be referred to as "step (1)"); (2) exposing the formed photoresist film by irradiating (via a liquid immersion medium, as needed) with a radioactive ray through a mask having a predetermined pattern (hereinafter, may be referred to as "step (2)"); heating the substrate (exposed photoresist film) (hereinafter, may be referred to as "step (3)"); and then (4) enabling a photoresist pattern to be formed when developed (hereinafter, may be referred to as "step (4)").

In the step (1), the radiation-sensitive resin composition, or a composition solution obtained by dissolving the same in a solvent is applied on a substrate (e.g., silicon wafer, wafer coated with silicon dioxide or an antireflection film, or the like) by an appropriate means for application such as spin-coating, cast coating, roll coating to form a photoresist film. Specifically, after the resin composition solution is applied such that a resulting resist film has a predetermined film thickness, the solvent in the coating film is evaporated by prebaking (PB) to form a resist film.

In the step (2), the photoresist film formed in the step (1) (if necessary, via a liquid immersion medium such as water), is exposed by irradiating with a radioactive ray. In this step, the radioactive ray is irradiated through a mask having a predetermined pattern. The radioactive ray appropriately selected from visible light rays, ultraviolet rays, deep ultraviolet rays, X-ray, charged particle ray and the like in accordance with the line width of the intended pattern may be irradiated. The radioactive ray is preferably far ultraviolet rays typified by ArF excimer laser light (wavelength: 193 nm) and KrF excimer laser light (wavelength: 248 nm) are preferred, and in particular, ArF excimer laser light is preferred.

The step (3) is referred to as "post exposure baking (PEB)", in which the acid generated from acid generator deprotects the resin (B) and the like at sites of the photoresist film exposed in the step (2). There arises the difference between the solubility of portions which were exposed (light-exposed site) and that of portions which were not exposed (light-unexposed site) in an alkaline developer. PEB is performed at an appropriately selected temperature from the range of usually 50° C. to 180° C.

In the step (4), the exposed photoresist film is developed with a developing solution to form a predetermined photoresist pattern. After the development, the film is, in general, washed with water, and then dried. The developing solution is preferably an alkali aqueous solution prepared by dissolving at least one alkaline compound such as, for example, sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo[5.4.0]-7-undecene, or 1,5-diazabicyclo[4.3.0]-5-nonene.

Alternatively, when liquid immersion lithography is carried out, a protective film for liquid immersion that is insoluble in the immersion liquid may be provided on the resist film prior to the step (2) so as to protect the resist film from being brought into direct contact with the immersion liquid. Any one of a protective film removable with solvent that is to be removed by a solvent prior to the step (4) (for example, see JP-A No. 2006-227632), and a protective film removable with developing solution that is to be removed during the development in the step (4) (for example, see PCT International Publication Nos. WO 2005-069076 and WO 2006-035790) may be used as the protective film for liquid immersion. It is preferable to use a protective film for liquid immersion removable with developing solution in light of throughput.

EXAMPLES

Hereinafter, embodiments of the present invention are more specifically described by way of Examples. However, these Examples should not be construed as in any way limiting the present invention. In Examples and Comparative Examples, the "part" is on mass basis unless otherwise stated particularly. Each measurement in Examples and Comparative Examples was conducted according to the following method.

Polystyrene Equivalent Weight Average Molecular Weight (Mw), and Polystyrene Equivalent Number Average Molecular Weight (Mn)

Mw and Mn were measured by gel permeation chromatography (GPC) using GPC columns manufactured by Tosoh Corporation (G2000HXL×2, G3000HXL×1, G4000HXL×1) under analysis conditions including a flow rate of 1.0 mL/min, an elution solvent of tetrahydrofuran, a column temperature of 40° C., with mono-disperse polystyrene as a standard.

$^1$H-NMR Analysis $^1$H-NMR analysis of the compound (A) was carried out for determination using a nuclear magnetic resonance equipment (trade name: JNM-ECX400, manufactured by JEOL Ltd.).

$^{13}$C-NMR Analysis $^{13}$C-NMR analysis of each polymer was carried out for determination using a nuclear magnetic resonance equipment (trade name: JNM-ECX400, manufactured by JEOL Ltd.).

<Synthesis of Compound (A)>

Example 1

Synthesis of Compound (A-1)

A solution in which 5 g of di-t-amylpyrocarbonate was dissolved in 5 mL of dichloromethane was provided. Into a 100 mL three-neck flask equipped with a thermometer and a dropping funnel were charged 1.87 g of 4-hydroxypiperidine, 3.73 g of triethylamine and 20 mL of dichloromethane, and the mixture was stirred in an ice bath, for 15 min. Thereto was added a di-t-amylpyrocarbonate solution dropwise which had been prepared beforehand using a dropping funnel over 5 min. After completing dropwise addition, the mixture was further stirred in an ice bath for 30 min, followed by removal from the ice bath. Then the mixture was stirred at room temperature for 7 hrs to complete the reaction.

After completing the reaction, the reaction solution was charged into a separatory funnel, and thereto was added 50 mL of a 1.0 mol/L aqueous acetic acid solution. The mixture was vigorously stirred, and then the oil layer was separately obtained. Further, an oily layer was separately obtained by a similar procedure was subjected to a treatment with an aqueous acetic acid solution. Thus resulting oil layer was washed with 100 mL of an aqueous saturated sodium bicarbonate solution. Thereafter, the oil layer was separately obtained, and then dried by adding thereto anhydrous magnesium sulfate. After the oil layer was dried, low-boiling point components were distilled away under reduced pressure, and silica gel column chromatography was carried out to isolate an N-t-amyloxycarbonyl-4-hydroxypiperidine (compound (A-1)) (3.1 g, yield: 77%).

As a result of $^1$H-NMR analysis, chemical shift of the compound (A-1) was as follows.

$^1$H-NMR (CDCl$_3$): δ 3.85 (3H), 3.03 (2H), 1.85 (2H), 1.76 (2H), 1.43 (8H), 0.89 (3H)

<Synthesis of Resin (B)>

Resins (B-1) to (B-3) as the resin (B) were synthesized in each Synthesis Example using monomers represented by the following formulae (M-1) to (M-6).

(M-1): 1-methylcyclopentyl methacrylate
(M-2): 1-ethyladamantyl methacrylate
(M-3): 4-oxa-5-oxotricyclo[4.2.1.0$^{3,7}$]nonane-2-yl methacrylate
(M-4): 1-ethylcyclopentyl methacrylate
(M-5): 1-i-propylcyclopentyl methacrylate
(M-6): 1,3-dioxa-2-oxocyclopentane-4-ylmethyl methacrylate

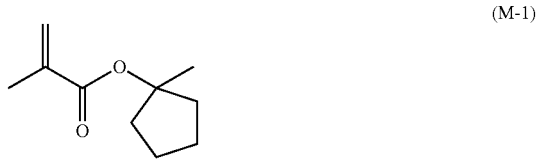

(M-1)

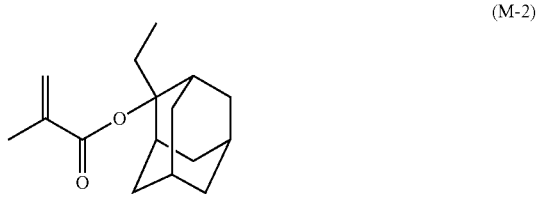

(M-2)

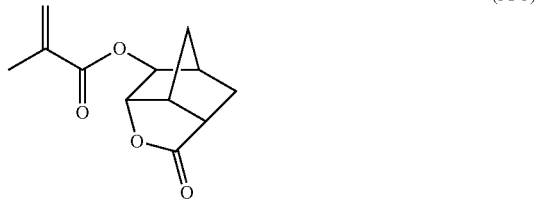

(M-3)

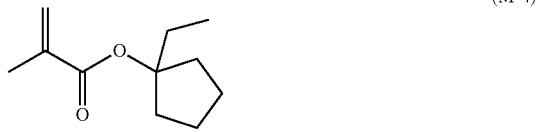

(M-4)

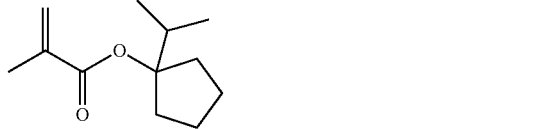

(M-5)

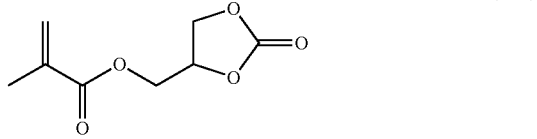

(M-6)

Synthesis Example 1

Synthesis of Resin (B-1)

A monomer solution was provided by dissolving 14.20 g (35% by mole) of the monomer (M-1), 8.99 g (15% by mole) of the monomer (M-2), and 26.81 g (50% by mole) of the monomer (M-3) in 100 g of 2-butanone, and further adding thereto 2.78 g of dimethyl 2,2'-azobis(2-methylpropionate) as an initiator.

Next, a 500 mL three-neck flask equipped with a thermometer and a dropping funnel was charged with 50 g of 2-butanone, and purged with nitrogen for 30 min. After the nitrogen purge, the interior of the flask was heated to 80° C. while stirring with a magnetic stirrer. The monomer solution which had been prepared beforehand was added dropwise using a dropping funnel over 3 hrs. The polymerization reaction was allowed for 6 hrs from the time point of initiation of addition of the monomer solution as the polymerization start time. After completion of the polymerization, the polymer solution was cooled with water to no higher than 30° C. After cooling, the polymer solution was added to 1,000 g of hexane, the deposited white powder was filtered off. The white powder thus filtered off was dissolved again in 200 g of 2-butanone, and added to 1,000 g of hexane, followed by filtering off the white powder thus deposited. Moreover, a similar operation was carried out again. Thereafter, the white powder obtained by filtering off was dried at 50° C. for 17 hrs to obtain a white powdery copolymer (38 g, yield: 75%). This copolymer was designated as resin (B-1).

This copolymer had Mw of 6,520, and Mw/Mn of 1.61. As a result of $^{13}$C-NMR analysis, the content (% by mole) of each of repeating units derived from the monomer (M-1), the monomer (M-2) and the monomer (M-3) was 35.5:15.3:49.2.

Synthesis Example 2

Synthesis of Resin (B-2)

A monomer solution was provided by dissolving 27.64 g (60% by mole) of the monomer (M-1), 10.19 g (20% by mole) of the monomer (M-6), and 12.17 g (20% by mole) of the monomer (M-3) in 100 g of 2-butanone, and further adding thereto 2.25 g of dimethylazobisisobutyronitrile as an initiator.

Next, a 500 mL three-neck flask equipped with a thermometer and a dropping funnel was charged with 50 g of 2-butanone, and purged with nitrogen for 30 min. After the nitrogen purge, the interior of the flask was heated to 80° C. while stirring with a magnetic stirrer. The monomer solution which had been prepared beforehand was added dropwise using a dropping funnel over 3 hrs. The polymerization reaction was allowed for 6 hrs from the time point of initiation of addition of the monomer solution as the polymerization start time. After completion of the polymerization, the polymer solution was cooled with water to no higher than 30° C. After cooling, the polymer solution was added to 1,000 g of hexane, the deposited white powder was filtered off. The white powder thus filtered off was dissolved again in 200 g of 2-butanone, and added to 1,000 g of hexane, followed by filtering off the white powder thus deposited. Moreover, a similar operation was carried out again. Thereafter, the white powder obtained by filtering off was dried at 50° C. for 17 hrs to obtain a white powdery copolymer (36 g, yield: 72%). This copolymer was designated as resin (B-2).

This copolymer had Mw of 6,720, and Mw/Mn of 1.52. As a result of $^{13}$C-NMR analysis, the content (% by mole) of each of repeating units derived from the monomer (M-1), the monomer (M-6) and the monomer (M-3) was 59.1:20.3:20.6.

Synthesis Example 3

Synthesis of Resin (B-3)

A monomer solution was provided by dissolving 22.82 g (50% by mole) of the monomer (M-4), 4.92 g (10% by mole) of the monomer (M-5), and 22.26 g (40% by mole) of the monomer (M-3) in 100 g of 2-butanone, and further adding thereto 1.15 g of dimethyl 2,2'-azobis(2-methylpropionate) as an initiator.

Next, a 500 mL three-neck flask equipped with a thermometer and a dropping funnel was charged with 50 g of 2-butanone, and purged with nitrogen for 30 min. After the nitrogen purge, the interior of the flask was heated to 80° C. while stirring with a magnetic stirrer. The monomer solution which had been prepared beforehand was added dropwise using a dropping funnel over 3 hrs. The polymerization reaction was allowed for 6 hrs from the time point of initiation of addition of the monomer solution as the polymerization start time. After completion of the polymerization, the polymer solution was cooled with water to no higher than 30° C. After cooling, the polymer solution was added to 1,000 g of hexane, the deposited white powder was filtered off. The white powder thus filtered off was dissolved again in 200 g of 2-butanone, and added to 1,000 g of hexane, followed by filtering off the white powder thus deposited. Moreover, a similar operation was carried out again. Thereafter, the white powder obtained by filtering off was dried at 50° C. for 17 hrs to obtain a white powdery copolymer (39 g, yield: 78%). This copolymer was designated as resin (B-3).

This copolymer had Mw of 11,320, and Mw/Mn of 1.57. As a result of $^{13}$C-NMR analysis, the content (% by mole) of each of repeating units derived from the monomer (M-4), the monomer (M-5) and the monomer (M-3) was 49.7:9.3:41.0.

<Synthesis of Resin (F)>

Fluorine-containing resins (resin (F)) included as an additive (E) to the radiation-sensitive resin compositions used in the following Examples and Comparative Examples were synthesized with compounds represented by the following formulae (S-1) to (S-5).

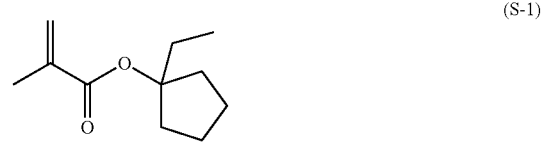

(S-1)

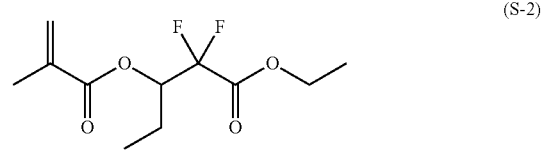

(S-2)

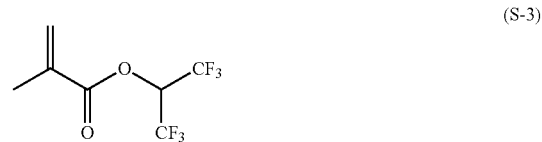

(S-3)

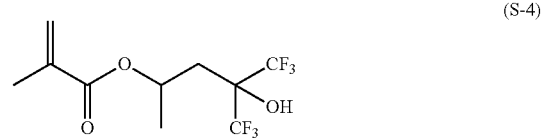

(S-4)

(S-5)

Synthesis Example 4

Synthesis of Polymer (F-1)

The compound (S-1) in an amount of 7.70 g (20% by mole), and 42.30 g (80% by mole) of the compound (S-2) were dissolved in 100 g of 2-butanone, and further 1.74 g of azobisisobutyronitrile was added thereto to provide a monomer solution. On the other hand, 500 mL three-necked flask charged with 50 g of 2-butanone, and purged with nitrogen for 30 min, followed by heating the reaction vessel to 80° C. while stirring. Subsequently, the monomer solution which had been prepared beforehand was added dropwise using a dropping funnel over 3 hrs. The polymerization reaction was allowed for 6 hrs from the time point of initiation of addition of the monomer solution as the polymerization start time.

After completion of the polymerization, the polymerization solution was cooled with water to no higher than 30° C., and the polymerization solution was transferred to a 2 L separatory funnel. The polymerization solution was diluted with 150 g of methanol, and thereto 600 g of hexane was added followed by mixing. Thereafter, 21 g of distilled water was added thereto and the mixture was further stirred and left to stand for 30 min. Thereafter, the underlayer was recovered to provide a propylene glycol monomethyl ether acetate solution. The yield of the solid content (polymer) of the propylene glycol monomethyl ether acetate solution was 71%. The Mw was 6,850, and the Mw/Mn was 1.38. As a result of $^{13}$C-NMR analysis, the content (% by mole) of the repeating units derived from the compound (S-1) and the compound (S-2) was 20.6:79.4, and the rate of the fluorine atom included was 12.1%. This copolymer was designated as resin (F-1).

<Synthesis of Polymer for Upper Layer Film>

As a component of a composition for forming an upper layer film for use in forming a protective film for liquid immersion in pattern formation in the following Examples and Comparative Examples, the polymer for an upper layer film described below was synthesized according to the following method.

Synthesis Example 5

Synthesis of Polymer for Upper Layer Film (1)

A monomer solution (i) containing 22.26 g of the compound (S-3) and 4.64 g of the 2,2-azobis(methyl 2-methylisopropionate) dissolved in 25 g of 2-butanone beforehand, and a monomer solution (ii) containing 27.74 g of the compound (S-4) dissolved in 25 g of 2-butanone beforehand were provided, respectively. On the other hand, a 500 mL three-necked flask equipped with a thermometer and a dropping funnel was charged with 100 g of 2-butanone, and purged with nitrogen for 30 min. After the nitrogen purge, the interior of the flask was heated to 80° C. while stirring with a magnetic stirrer.

The monomer solution (i) which had been prepared beforehand was added dropwise using a dropping funnel over 20 min, and aging was allowed for 20 min. Subsequently, dropwise addition of the monomer solution (ii) over 20 min followed. Thereafter, the reaction was allowed for additional 1 hour, and cooling to no higher than 30° C. gave a copolymerization solution. Thus resulting copolymerization solution was concentrated to 150 g, and thereafter transferred to a separatory funnel. This separatory funnel was charged with 50 g of methanol and 400 g of n-hexane, and separation purification was performed. After the separation, the underlayer liquid was recovered. The underlayer liquid thus recovered was replaced with 4-methyl-2-pentanol to give a resin solution. The copolymer contained in the resulting resin solution had Mw of 5,730, and Mw/Mn of 1.23, with the yield being 26%. Also, the content (% by mole) of each of repeating units derived from the compound (S-3) and the compound (S-4) was 50.3:49.7, and the rate of the fluorine atom included was 43.6%. This copolymer was designated as polymer for an upper layer film (1).

Synthesis Example 6

Synthesis of Polymer for Upper Layer Film (2)

A monomer solution containing 46.95 g (85% by mole) of the compound (S-4), and 6.91 g of 2,2'-azobis-(methyl 2-methylpropionate) dissolved in 100 g of isopropyl alcohol was provided. On the other hand, a 500 mL three-necked flask equipped with a thermometer and a dropping funnel was charged with 50 g of isopropyl alcohol, and purged with nitrogen for 30 min. After the nitrogen purge, the interior of the flask was heated to 80° C. while stirring with a magnetic stirrer. The monomer solution which had been prepared beforehand was added dropwise using a dropping funnel over 2 hrs.

After the completion of the dropwise addition, the reaction was allowed for additional 1 hour, and thereto was added 10 g of an isopropyl alcohol solution prepared by dissolving 3.05 g (15% by mole) of the compound (S-5) over 30 min, followed by allowing for the reaction for additional 1 hour. The mixture was cooled to no higher than 30° C. to give a copolymerization solution. After the resulting copolymerization solution was concentrated to 150 g, it was transferred to a separatory funnel. This separatory funnel was charged with 50 g of methanol and 600 g of n-hexane, and separation purification was performed. After the separation, the underlayer liquid was recovered. The underlayer liquid thus recovered was diluted with isopropyl alcohol to 100 g, and again transferred to a separatory funnel. The separatory funnel was charged with 50 g of methanol and 600 g of n-hexane, and separation purification was performed. After the separation, the underlayer liquid was recovered. The underlayer liquid thus recovered was replaced with 4-methyl-2-pentanol, thereby adjusting the total amount to 250 g. After the adjustment, 250 g of water was added thereto, and separation purification was performed. After the separation, the upper layer liquid was recovered.

The upper layer liquid thus recovered was replaced with 4-methyl-2-pentanol to give a resin solution. The copolymer contained in the resulting resin solution had Mw of 9,760, and Mw/Mn of 1.51, with the yield being 65%. Also, the content (% by mole) of each of repeating units derived from the compound (S-4) and the compound (S-5) was 95.0:5.0, and the rate of the fluorine atom included was 36.8%. This copolymer was designated as polymer for an upper layer film (2).

<Preparation of Composition for Forming Upper Layer Film (H)>

A composition for forming an upper layer film (H) for use in forming a protective film for liquid immersion in pattern formation in the following Examples and Comparative Examples was prepared according to the method described below using the polymer for an upper layer film obtained by the synthesis as described above.

Synthesis Example 7

Preparation of Composition for Forming Upper Layer Film (H)

A composition for forming an upper layer film (H) was prepared by mixing 7 parts by mass of the polymer for an upper layer film (1) prepared in Synthesis Example 5, 93 parts by mass of the polymer for an upper layer film (2) prepared in Synthesis Example 6, 10 parts by mass of diethylene glycol monoethyl ether acetate, 10 parts by mass of 4-methyl-2-hexanol, and 90 parts by mass of diisoamyl ether.

<Preparation of Radiation-Sensitive Resin Composition>

Each component for constituting the radiation-sensitive resin composition other than the compound (A), the resin (B) and the resin (F) synthesized in the foregoing Examples and Synthesis Examples (nitrogen-containing compounds other than the compound (A), acid generators (C) and solvents (D)) is shown below.

<Nitrogen-Containing Compound Other than Compound (A)>

(a-1): N-t-butoxycarbonyl-4-hydroxypiperidine (a-2): 2-phenylbenzimidazole (a-3): 2,6-diisopropyl aniline <Acid Generator (C)>

(C-1): triphenylsulfonium 2-(bicyclo[2.2.1]hept-2-yl)-1,1-difluoroethanesulfonate (compound represented by the following formula (C-1))

(C-2): triphenylsulfonium 2-(adamantan-1-yl)-1,1-difluoroethanesulfonate (compound represented by the following formula (C-2))

(C-3): 4-cyclohexylphenyl-diphenylsulfonium nonafluoro-n-butanesulfonate (compound represented by the following formula (C-3))

(C-4): triphenylsulfonium 6-(adamantan-1-ylcarbonyloxy)-1,1,2,2-tetrafluorohexanesulfonate (compound represented by the following formula (C-4))

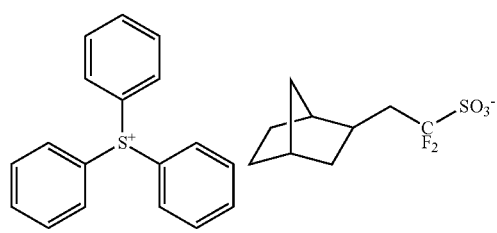

(C-1)

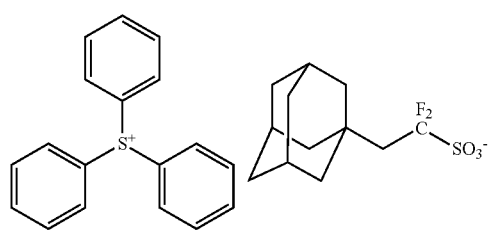

(C-2)

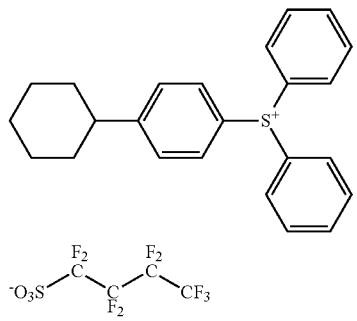

(C-3)

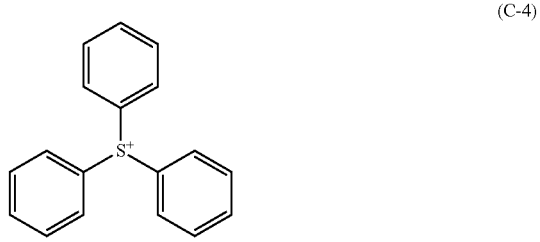

(C-4)

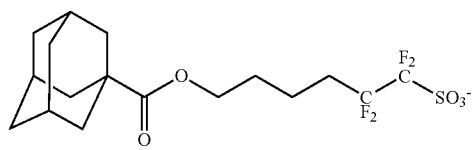

<Solvent (D)>

(D-1): propylene glycol monomethyl ether acetate (D-2): cyclohexanone (D-3): γ-butyrolactone

Example 2

A radiation-sensitive resin composition was prepared by: mixing 0.7 parts by mass of the compound (A-1) (N-t-amyloxycarbonyl-4-hydroxypiperidine), 100 parts by mass of the resin (B-1) obtained in Synthesis Example 1, and 7.5 parts by mass of (C-1) (triphenylsulfonium 2-bicyclo[2.2.1]hept-2-yl-1,1-difluoroethanesulfonate) as the acid generator (C); adding to the mixture as the solvent (D), 1,500 parts by mass of (D-1) propylene glycol monomethyl ether acetate, 650 parts by mass of (D-2)cyclohexanone and 30 parts by mass of (D-3)γ-butyrolactone; allowing for dissolution of the mixture to give a mixed solution; and filtering thus resulting mixed solution through a filter having a pore size of 0.20 μm.

Examples 3 to 5, and Comparative Examples 1 to 3

Radiation-sensitive resin compositions were prepared in a similar manner to Example 2 except that the amount of blended each component for constituting the radiation-sensitive resin composition (the amount of the resin (B) being assumed to be 100 parts by mass) was changed as shown in Table 1 below.

TABLE 1

| | Compound (A)/nitrogen-containing compound | | Resin (B) | Acid generator (C) | | Solvent (D) | | Resin (F) | |
|---|---|---|---|---|---|---|---|---|---|
| | Type | parts by mass | Type | Type | parts by mass | Type | parts by mass | Type | parts by mass |
| Example 2 | A-1 | 0.7 | B-1 | C-1 | 7.5 | D-1 | 1500 | — | — |
| | | | | | | D-2 | 650 | | |
| | | | | | | D-3 | 30 | | |
| Example 3 | A-1 | 0.37 | B-1 | C-1 | 7.5 | D-1 | 1500 | — | — |
| | a-2 | 0.33 | | | | D-2 | 650 | | |
| | | | | | | D-3 | 30 | | |
| Example 4 | A-1 | 1.34 | B-2 | C-2 | 10.4 | D-1 | 1800 | — | — |
| | | | | C-4 | 3.9 | D-2 | 770 | | |
| | | | | | | D-3 | 30 | | |
| Example 5 | A-1 | 0.51 | B-3 | C-2 | 6.0 | D-1 | 1800 | F-1 | 5.0 |
| | a-3 | 0.45 | | C-3 | 6.0 | D-2 | 770 | | |
| | | | | | | D-3 | 0 | | |
| Comparative Example 1 | a-1 | 0.7 | B-1 | C-1 | 7.5 | D-1 | 1500 | — | — |
| | | | | | | D-2 | 650 | | |
| | | | | | | D-3 | 30 | | |
| Comparative Example 2 | a-1 | 1.43 | B-2 | C-2 | 10.4 | D-1 | 1800 | — | — |
| | | | | C-4 | 3.9 | D-2 | 770 | | |
| | | | | | | D-3 | 30 | | |
| Comparative Example 3 | a-1 | 0.55 | B-3 | C-2 | 6.0 | D-1 | 1800 | F-1 | 5.0 |
| | a-3 | 0.45 | | C-3 | 6.0 | D-2 | 770 | | |
| | | | | | | D-3 | 0 | | |

[Evaluation]

The radiation-sensitive resin compositions obtained in Examples 2 to 5 and Comparative Examples 1 to 3 were evaluated for sensitivity, EL, and MEEF with a light source for ArF excimer laser. On each of Examples and Comparative Examples, patterns were formed according to the pattern-forming method shown in Table 2 among the Pattern-Forming Methods (P-1) to (P-3) explained in the following, and evaluations were made.

Pattern-Forming Method (P-1)

An underlayer antireflection film having a film thickness of 77 nm was formed on the surface of a 8 inch silicon wafer using an agent for forming underlayer antireflective coating (trade name "ARC29A", manufactured by Nissan Chemical Industries, Ltd.). On the surface of this substrate was applied the radiation-sensitive resin composition by spin coating, and SB (Soft Bake) was carried out on a hot plate at 100° C. for 60 sec to form a photoresist film having a film thickness of 120 nm.

This photoresist film was exposed through a mask pattern using a full field stepper (trade name "NSRS306C", manufactured by Nikon Corporation). Thereafter, post exposure baking (PEB) was carried out at 100° C. for 60 sec, and then the film was developed with a 2.38% aqueous tetramethylammonium hydroxide solution (hereinafter, also referred to as "aqueous TMAH solution") at 25° C. for 60 sec, washed with water and dried to form a positive type resist pattern. It should be noted that this positive type resist pattern was line-and-space of 1:1 with a line width of 90 nm formed through a mask for forming a target dimension of 90 nm with line-and-space of 1:1. For line-width measurement of the resist pattern formed by this method, a scanning electron microscope (trade name "S9260A", manufactured by Hitachi High-Technologies Corporation) was used. This pattern-forming method is designated as (P-1).

Pattern-Forming Method (P-2)

A photoresist film having a film thickness of 75 nm was formed using the radiation-sensitive resin composition on a 12 inch silicon wafer having an underlayer antireflection film which had been formed similarly to Pattern-Forming Method (P-1), and soft baking (SB) was carried out at 100° C. for 60 sec. Next, the composition for forming an upper layer film (H) was spin coated on the photoresist film thus formed, and subjected to PB (90° C., for 60 sec) to form a an upper layer film having a film thickness of 90 nm. Thereafter, exposure was carried out through a mask pattern using an ArF excimer laser immersion scanner (trade name "NSR S610C", manufactured by Nikon Corporation) under conditions of NA=1.3, ratio=0.800, and setting of "annular". After the exposure, post exposure baking (PEB) was carried out at 95° C. for 60 sec. Thereafter, development with a 2.38% aqueous TMAH solution, followed by washing with water and drying resulted in formation of a positive type resist pattern. It should be noted that this positive type resist pattern was line-and-space of 1:1 with a line width of 50 nm formed through a mask for forming a target dimension with a line of 50 nm and a pitch of 100 nm. For line-width measurement of the resist pattern formed by this method, a scanning electron microscope (trade name "CG-4000", manufactured by Hitachi High-Technologies Corporation) was used.

Pattern-Forming Method (P-3)

A photoresist film having a film thickness of 75 nm was formed using the radiation-sensitive resin composition on a 12 inch silicon wafer having an underlayer antireflection film which had been formed similarly to Pattern-Forming Method (P-1), and SB was carried out at 100° C. for 60 sec. Next, this photoresist film was subjected to exposure through a mask pattern using the ArF excimer laser immersion scanner under conditions of NA=1.3, ratio=0.800, and setting of "annular". After the exposure, post exposure baking (PEB) was carried out at 85° C. for 60 sec. Thereafter, development with a 2.38% aqueous TMAH solution, followed by washing with water and drying resulted in formation of a positive type resist pattern. It should be noted that this positive type resist pattern was line-and-space of 1:1 with a line width of 50 nm formed through a mask for forming a target dimension with a line of 50 nm and a pitch of 100 nm. For line-width measurement of the resist pattern formed by this method, a scanning electron microscope ("CG-4000", manufactured by Hitachi High-Technologies Corporation) was used.

Each evaluation was made according to the following method. The results thus obtained are shown in Table 2.

Sensitivity

In the case of the aforementioned Pattern-Forming Method (P-1), the exposure dose (mJ/cm$^2$) at which the line width formed through the mask for a dimension of 90 nm with line-and-space of 1:1 resulted in formation of line-and-space of 1:1 with a line width of 90 nm was defined as an optimal exposure dose, and this optimal exposure dose (mJ/cm$^2$) was designated as "sensitivity". Similarly, in the cases of the Pattern-Forming Methods (P-2) and (P-3), the line width formed through the mask for a dimension of 50 nm with line-and-space of 1:1 resulted in formation of line-and-space of 1:1 with a line width of 50 nm was defined as an optimal exposure dose, and this optimal exposure dose (mJ/cm$^2$) was designated as "sensitivity".

Exposure Latitude (EL)

In the case of the Pattern-Forming Method (P-1), a ratio of the optimal exposure dose with respect to the range of the exposure dose when the pattern dimension resolved with the mask pattern of 90 nm 1 L/1 S fell within the range of ±10% of the designed dimension of the mask was defined as exposure latitude (EL). Similarly, in the cases of the Pattern-Forming Methods (P-2) and (P-3), a ratio of the optimal exposure dose with respect to the range of the exposure dose when the pattern dimension resolved with the mask pattern of 50 nm 1 L/1 S fell within the range of ±10% of the designed dimension of the mask was defined as exposure latitude (EL). It is desired that this value be as large as possible. For the observation of the pattern dimension, the scanning electron microscope described above was used.

MEEF

Using the scanning electron microscope described above, pattern dimensions resolved with three types of mask sizes (85.0 mL/170 nmP, 90.0 mL/180 nmP and 95.0 mL/190 nmP) were determined at the optimal exposure dose, in the case of the Pattern-Forming Method (P-1). The measurement results were plotted for the line width along the ordinate with respect to the mask size along the abscissa. The slope of the graph was determined according to a least squares method. In the cases of the Pattern-Forming Methods (P-2) and (P-3), pattern dimensions resolved with three types of mask sizes (46.0 mL/92 nmP, 50.0 mL/100 nmP and 54.0 mL/108 nmP) were determined in a similar manner. The measurement results were plotted for the line width along the ordinate with respect to the mask size along the abscissa. The slope of the graph was determined according to a least squares method, and this slope was designated as MEEF. It is desired that this value be as small as possible.

TABLE 2

| | Film-forming condition | | Pattern-forming method | Evaluation results | | |
|---|---|---|---|---|---|---|
| | SB (°C.) | PEB (°C.) | | Sensitivity | EL | MEEF |
| Example 2 | 100 | 100 | P-1 | 43.1 | 13.3 | 1.26 |
| Example 3 | 100 | 100 | P-1 | 42.9 | 13.1 | 1.29 |
| Example 4 | 100 | 95 | P-2 | 25.4 | 15.4 | 1.18 |
| Example 5 | 100 | 85 | P-3 | 27.3 | 16.1 | 1.21 |

TABLE 2-continued

| | Film-forming condition | | Pattern-forming method | Evaluation results | | |
|---|---|---|---|---|---|---|
| | SB (°C.) | PEB (°C.) | | Sensitivity | EL | MEEF |
| Comparative Example 1 | 100 | 100 | P-1 | 42.6 | 12.0 | 1.42 |
| Comparative Example 2 | 100 | 95 | P-2 | 25.2 | 15.7 | 1.27 |
| Comparative Example 3 | 100 | 85 | P-3 | 27.6 | 16.0 | 1.34 |

The radiation-sensitive resin composition of the embodiment of the present invention can be used in manufacturing process of semiconductors such as IC, production of circuit boards of liquid crystal, thermal head etc., and other photolithography process. Also the compound of the embodiment of the present invention can be suitably used as a constitutional component of the radiation-sensitive resin composition. More specifically, the radiation-sensitive resin composition of the embodiment of the present invention can be used as a chemically amplified radiation-sensitive resin composition which can be suitably used in photolithography process which is carried out using an exposure light source for electron beams as well as far ultraviolet rays with wavelengths of no greater than 250 nm such as KrF excimer laser and ArF excimer laser, and the like.

The radiation-sensitive resin composition of the embodiment of the present invention can be suitably used as a lithography material for processing with light such as KrF excimer laser and ArF excimer laser. In addition, the radiation-sensitive resin composition of the present invention is also applicable to liquid immersion lithography.

Obviously, numerous modifications and variations of the present invention are possible in light of the above teachings. It is therefore to be understood that within the scope of the appended claims, the invention may be practiced otherwise than as specifically described herein.

The invention claimed is:

1. A radiation-sensitive resin composition comprising:
   a compound represented by a following formula (1-1);
   a resin having an acid-dissociative dissolution-controlling group and a property such that alkali solubility of the resin increases by an action of an acid; and
   a radiation-sensitive acid generator,

(1-1)

wherein, in the formula (1-1), Y is a monovalent group having 5 to 20 carbon atoms and represented by a following formula (i), and R$^4$ and R$^5$ taken together represent a monovalent heterocyclic group having 4 to 20 carbon atoms together with the nitrogen atom to which R$^4$ and R$^5$ are attached, a part or all of the hydrogen atoms included in the monovalent heterocyclic group being substituted with a hydroxyl group, a carboxyl group, a —COOR group, a —OCOR group or a cyano group, wherein R represents an alkyl group having 1 to 10 carbon atoms,

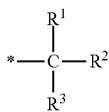

wherein, in the formula (i),
R¹ and R² each independently represent a linear or branched alkyl group having 1 to 4 carbon atoms or a monovalent alicyclic hydrocarbon group having 4 to 12 carbon atoms, or R¹ and R² are linked with each other to form a bivalent alicyclic hydrocarbon group having 4 to 12 carbon atoms together with the carbon atom to which R¹ and R² are attached,
R³ represents a linear or branched alkyl group having 1 to 4 carbon atoms or a monovalent alicyclic hydrocarbon group having 4 to 12 carbon atoms, and
"*" represents a bonding hand with the oxygen atom to which Y is bound.

2. The radiation-sensitive resin composition according to claim 1, wherein Y in the formula (1-1) is a t-amyl group.

3. The radiation-sensitive resin composition according to claim 1, wherein the resin has a repeating unit represented by a following formula (3),

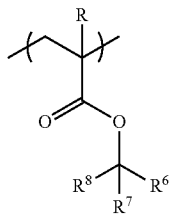

wherein, in the formula (3),
R represents a hydrogen atom or a methyl group,
R⁶ and R⁷ each independently represent a linear or branched alkyl group having 1 to 4 carbon atoms or a monovalent alicyclic hydrocarbon group having 4 to 20 carbon atoms, or R⁶ and R⁷ are linked with each other to form a bivalent alicyclic hydrocarbon group having 4 to 20 carbon atoms together with the carbon atom to which R⁶ and R⁷ are attached, and R⁸ represents a linear or branched alkyl group having 1 to 4 carbon atoms or a monovalent alicyclic hydrocarbon group having 4 to 20 carbon atoms.

4. The radiation-sensitive resin composition according to claim 1, wherein the resin has a repeating unit that includes a lactone skeleton, a cyclic carbonate skeleton or a combination thereof.

5. The radiation-sensitive resin composition according to claim 1, wherein R⁴ and R⁵ taken together represent a substituted or unsubstituted pyrrole, a substituted or unsubstituted imidazole, a substituted or unsubstituted pyrazole, a substituted or unsubstituted pyrrolidine, a substituted or unsubstituted piperidine, a substituted or unsubstituted piperazine or a substituted or unsubstituted morpholine together with the nitrogen atom to which R⁴ and R⁵ are attached.

6. A compound represented by a following formula (I-1), and having a molecular weight of no greater than 3,000,

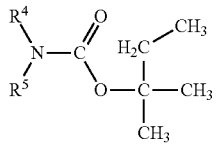

wherein, in the formula (I-1), R⁴ and R⁵ taken together represent a monovalent heterocyclic group having 4 to 20 carbon atoms together with the nitrogen atom to which R⁴ and R⁵ are attached, a part or all of the hydrogen atoms included in the monovalent heterocyclic group being substituted with a hydroxyl group, a carboxyl group, a —COOR group, a —OCOR group or a cyano group, wherein R represents an alkyl group having 1 to 10 carbon atoms.

7. The compound according to claim 6, wherein R⁴ and R⁵ taken together represent a substituted or unsubstituted pyrrole, a substituted or unsubstituted imidazole, a substituted or unsubstituted pyrazole, a substituted or unsubstituted pyrrolidine, a substituted or unsubstituted piperidine, a substituted or unsubstituted piperazine or a substituted or unsubstituted morpholine together with the nitrogen atom to which R⁴ and R⁵ are attached.

* * * * *